US012653498B2

(12) United States Patent
Niwamae et al.

(10) Patent No.: US 12,653,498 B2
(45) Date of Patent: Jun. 16, 2026

(54) ULTRASONIC DIAGNOSIS APPARATUS

(71) Applicant: CANON KABUSHIKI KAISHA, Tokyo (JP)

(72) Inventors: Yuki Niwamae, Kanagawa (JP); Sakiko Tanimoto, Shizuoka (JP); Takahiro Yamamoto, Kanagawa (JP); Satoshi Shinata, Kanagawa (JP); Yusuke Hokari, Tokyo (JP); Shosaku Kawashima, Kanagawa (JP); Yoshinori Hirano, Chiba (JP); Akiya Nakayama, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 18/614,374

(22) Filed: Mar. 22, 2024

(65) Prior Publication Data

US 2024/0225594 A1 Jul. 11, 2024

Related U.S. Application Data

(63) Continuation of application No. PCT/JP2022/035400, filed on Sep. 22, 2022.

(30) Foreign Application Priority Data

Sep. 27, 2021 (JP) ................................. 2021-157066

(51) Int. Cl.
*A61B 8/00* (2006.01)

(52) U.S. Cl.
CPC ................ *A61B 8/40* (2013.01); *A61B 8/462* (2013.01); *A61B 8/467* (2013.01)

(58) Field of Classification Search
CPC ....... A61B 8/40; A61B 8/4263; A61B 8/4411; A61B 8/4433; A61B 8/462; A61B 8/467
See application file for complete search history.

(56) References Cited

U.S. PATENT DOCUMENTS

| | | | |
|---|---|---|---|
| 6,716,167 B1 | 4/2004 | Henderson | |
| 9,980,703 B2 * | 5/2018 | Wodecki | A61B 8/4427 |
| 10,322,682 B2 * | 6/2019 | Faist | B60K 35/10 |
| 2010/0152589 A1 * | 6/2010 | Asai | A61B 50/10 |
| | | | 600/459 |
| 2011/0283632 A1 * | 11/2011 | Sutton | A47B 46/005 |
| | | | 52/36.1 |
| 2015/0272502 A1 * | 10/2015 | Kaku | A61B 8/4444 |
| | | | 600/407 |

(Continued)

FOREIGN PATENT DOCUMENTS

| | | |
|---|---|---|
| CN | 104840177 A | 8/2015 |
| CN | 204636288 U | 9/2015 |

(Continued)

*Primary Examiner* — Christopher L Cook
(74) *Attorney, Agent, or Firm* — Canon U.S.A., Inc. IP Division

(57) ABSTRACT

Provided is an ultrasonic diagnosis apparatus with improved operability. An ultrasonic diagnosis apparatus according to the present invention includes an operation unit that includes a plurality of input components, and is configured to input at least information regarding an ultrasonic wave, a bed unit on which a subject is to be placed, and a support unit configured to support the operation unit and the bed unit in such a manner that the operation unit is arranged superior to the bed unit.

19 Claims, 13 Drawing Sheets

(56)             References Cited

U.S. PATENT DOCUMENTS

| 2018/0055485 | A1 | | 3/2018 | Lalena |
| 2019/0307423 | A1 | | 10/2019 | Han |
| 2019/0307628 | A1 | | 10/2019 | Park |
| 2020/0000430 | A1 | * | 1/2020 | Chamberlain ......... A61B 8/467 |

FOREIGN PATENT DOCUMENTS

| CN | 205433739 | U | | 8/2016 |
| CN | 210521550 | U | | 5/2020 |
| JP | H0938073 | A | | 2/1997 |
| JP | 2002542870 | A | | 12/2002 |
| JP | 2009178346 | A | | 8/2009 |
| JP | 2009189633 | A | | 8/2009 |
| JP | 2009240342 | | * | 10/2009 |
| JP | 2009240342 | A | | 10/2009 |
| JP | 2010046374 | A | | 3/2010 |
| JP | 2013048740 | A | | 3/2013 |
| KR | 20150052673 | A | | 5/2015 |
| WO | 2016148872 | A1 | | 9/2016 |

* cited by examiner

ULTRASONIC DIAGNOSIS APPARATUS

CROSS-REFERENCE TO RELATED APPLICATIONS

This application is a Continuation of International Patent Application No. PCT/JP2022/035400, filed Sep. 22, 2022, which claims the benefit of Japanese Patent Application No. 2021-157066, filed Sep. 27, 2021, both of which are hereby incorporated by reference herein in their entirety.

BACKGROUND OF THE INVENTION

Field of the Invention

The present invention relates to an ultrasonic diagnosis apparatus that generates an ultrasonic image by transmitting and receiving ultrasonic waves to and from a subject.

Background Art

The conventional ultrasonic diagnosis apparatus generates an ultrasonic image by bringing an ultrasonic probe into contact with a subject placed on a bed provided separately from an apparatus main body of the ultrasonic diagnosis apparatus, and the apparatus main body processing an ultrasonic signal received by the ultrasonic probe. Then, a display unit of the ultrasonic diagnosis apparatus displays the ultrasonic image, a measurement result, and the like. An ultrasonic diagnosis apparatus that can install a display unit at a position at which an operator can easily view an ultrasonic image is discussed (for example, Patent Literature 1).

CITATION LIST

Patent Literature

PTL 1: Japanese Patent Application Laid-Open No. 2010-46374

In the ultrasonic diagnosis apparatus discussed in Patent Literature 1, an operation unit to be operated by an operator is installed on an ultrasonic diagnosis apparatus separated from a bed on which a subject is placed. Because the operator operates the operation unit while bringing an ultrasonic probe into contact with a subject placed on the bed, the operator has sometimes captured an image of the subject in an unnatural posture.

SUMMARY OF THE INVENTION

To solve the above-described problem, an ultrasonic diagnosis apparatus according to the present invention includes an operation unit that includes a plurality of input components, and is configured to input at least information regarding an ultrasonic wave, a bed unit on which a subject is to be placed, and a support unit configured to support the operation unit and the bed unit in such a manner that the operation unit is arranged superior to the bed unit.

The ultrasonic diagnosis apparatus according to the present invention may include a display unit configured to display an ultrasonic image that is based on an ultrasonic wave transmitted and received using an ultrasonic probe that transmits and receives ultrasonic waves to and from a subject, and the support unit may support the display unit and the bed unit in such a manner that the display unit is arranged superior to the bed unit.

The support unit may be a member extending in an up-down direction.

The support unit may support the bed unit and the operation unit in such a manner that the bed unit and the operation unit are separated in an up-down direction.

The support unit may support the bed unit and the display unit in such a manner that the bed unit and the display unit are separated in an up-down direction.

The support unit may have a cantilever structure of supporting the operation unit and the bed unit in such a manner that the operation unit and the bed unit protrude toward one direction.

The operation unit may be supported on the support unit via an arm.

The arm may be extendable and contractible.

The ultrasonic diagnosis apparatus according to the present invention may include a panel unit including the operation unit and the display unit.

The panel unit and the bed unit may be movable in an up-down direction.

The ultrasonic diagnosis apparatus according to the present invention may include a coupling unit configured to couple between the panel unit and the bed unit, and the coupling unit may be supported movably in an up-down direction relative to the support unit.

The operation unit may be installed on the panel unit via an arm.

The arm may be installed on the panel unit via a first hinge portion, the operation unit may be installed on the arm via a second hinge portion, and by folding the arm, the operation unit may be accommodated in the panel unit.

The first hinge portion may be a torque hinge that can stop the arm at an arbitrary position.

The panel unit may include an ultrasonic probe holder for placing the ultrasonic probe, and a bottle accommodation unit that accommodates a bottle of ultrasound gel.

The display unit may be installed rotatably relative to the panel unit.

The operation unit may be detachably installed on the panel unit.

An ultrasonic diagnosis apparatus according to the present invention includes a display unit configured to display an ultrasonic image that is based on an ultrasonic wave transmitted and received using an ultrasonic probe that transmits and receives ultrasonic waves to and from a subject, a bed unit on which the subject is to be placed, and a support unit configured to support the display unit and the bed unit in such a manner that the display unit is arranged superior to the bed unit.

Further features of the present invention will become apparent from the following description of exemplary embodiments with reference to the attached drawings.

DESCRIPTION OF THE EMBODIMENTS

An ultrasonic diagnosis apparatus according to the present invention includes an ultrasonic probe configured to perform transmission and reception of ultrasonic waves by being brought into contact with a subject, an operation unit that includes a plurality of input components, and is configured to input at least information regarding ultrasonic waves, a bed unit on which a subject is to be placed, and a display unit configured to display an ultrasonic image generated by an ultrasonic signal received by the ultrasonic probe being processed, a measurement result, and the like.

The ultrasonic diagnosis apparatus according to the present invention includes a support unit configured to support each component of the ultrasonic diagnosis apparatus. The support unit virtually-movably supports the operation unit and the bed unit, and also virtually-movably supports the display unit and the bed unit. The ultrasonic diagnosis apparatus according to the present invention also includes an accommodation unit configured to accommodate a plurality of ultrasonic probes. The support unit supports the accommodation unit.

The ultrasonic diagnosis apparatus according to the present invention can also be rephrased as an ultrasonic diagnosis apparatus, an ultrasonic diagnosis system, or an ultrasonic imaging system that is equipped with a bed unit.

Hereinafter, a preferred exemplary embodiment of the present invention will be described with reference to the accompanying drawings.

Figure 1:
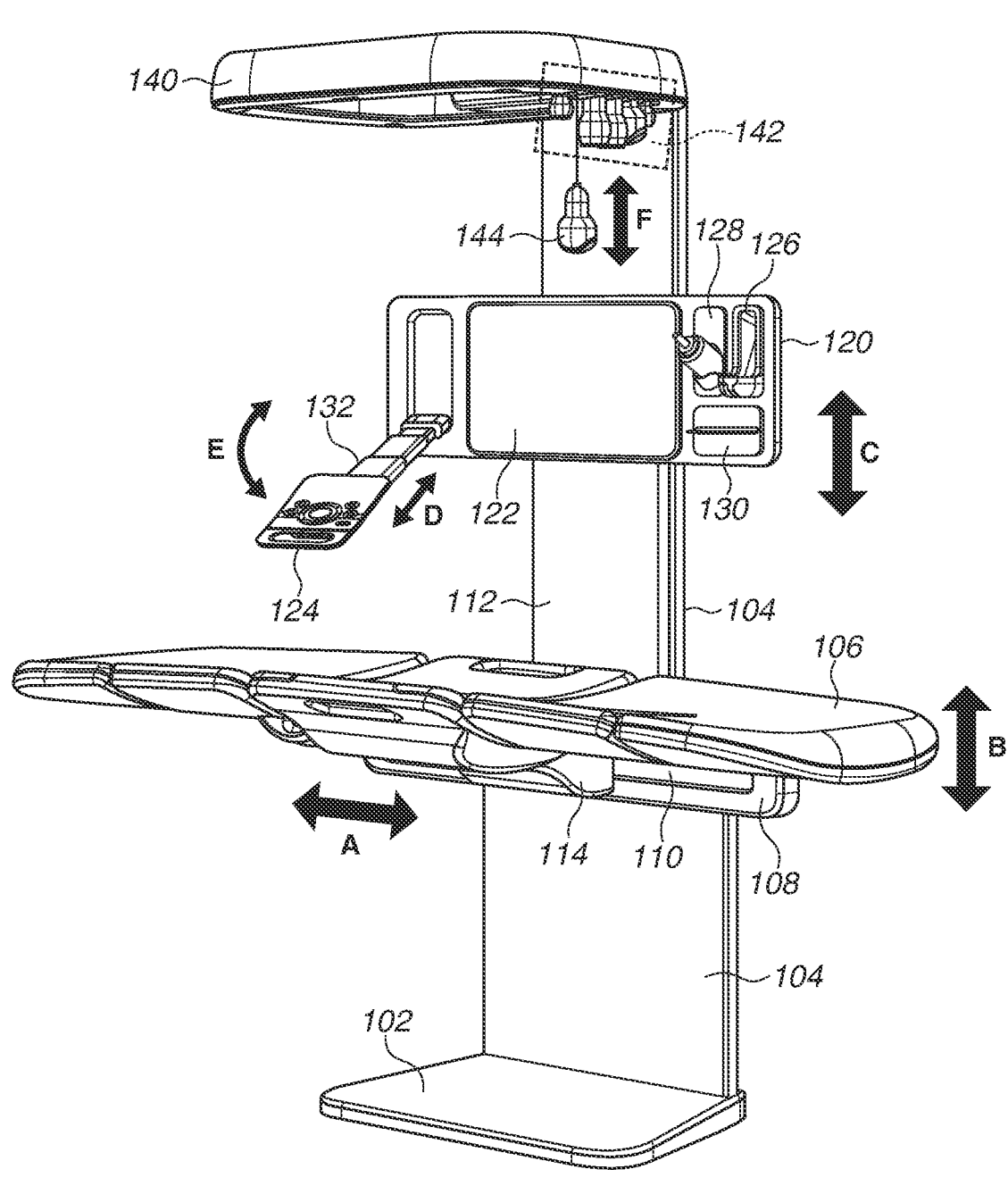
FIG. 1 is a perspective view illustrating a configuration of an ultrasonic diagnosis apparatus according to the present invention.
Figure 2:
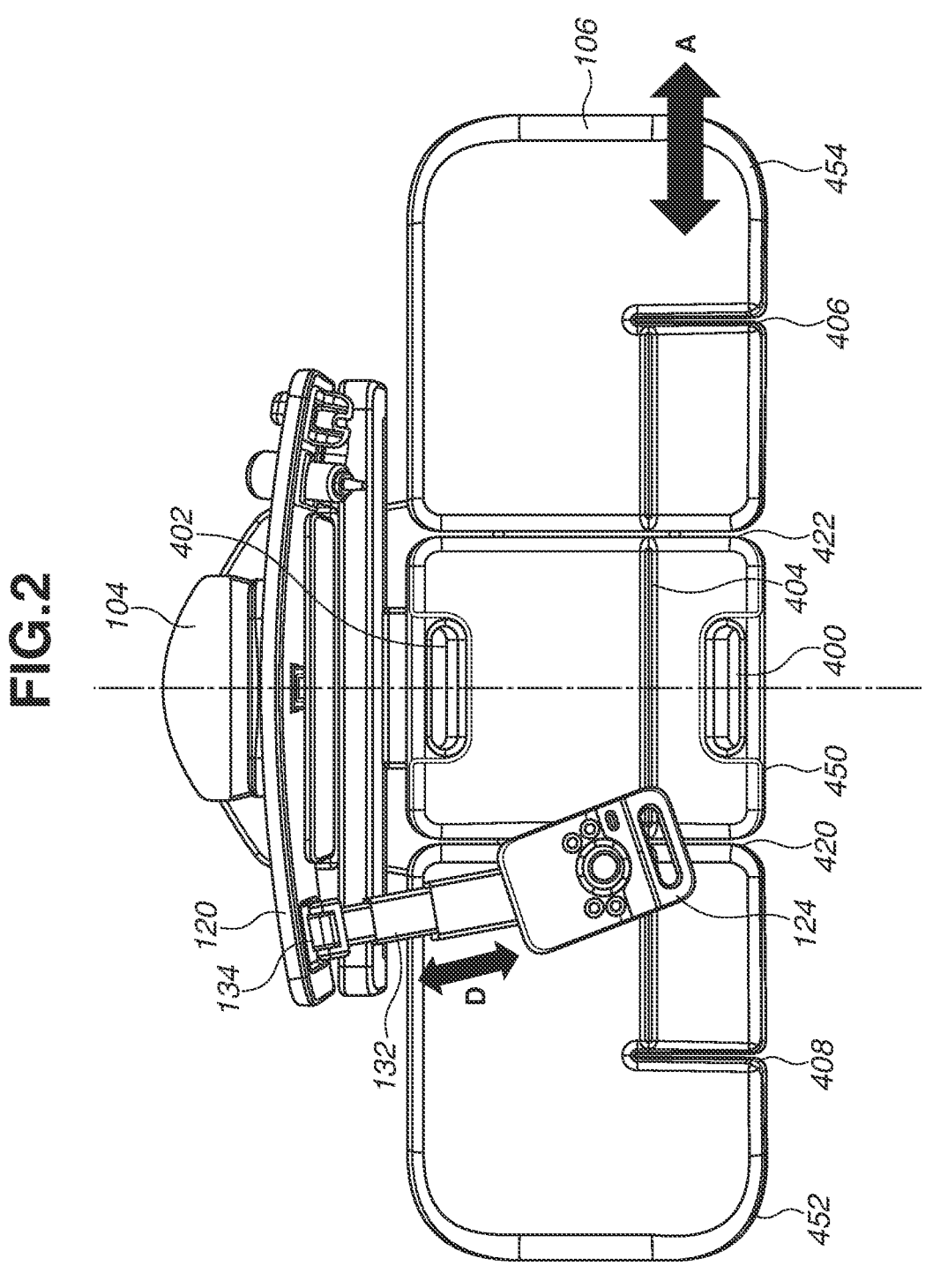
FIG. 2 is a top view illustrating a configuration of an ultrasonic diagnosis apparatus according to the present invention.
Figure 3:
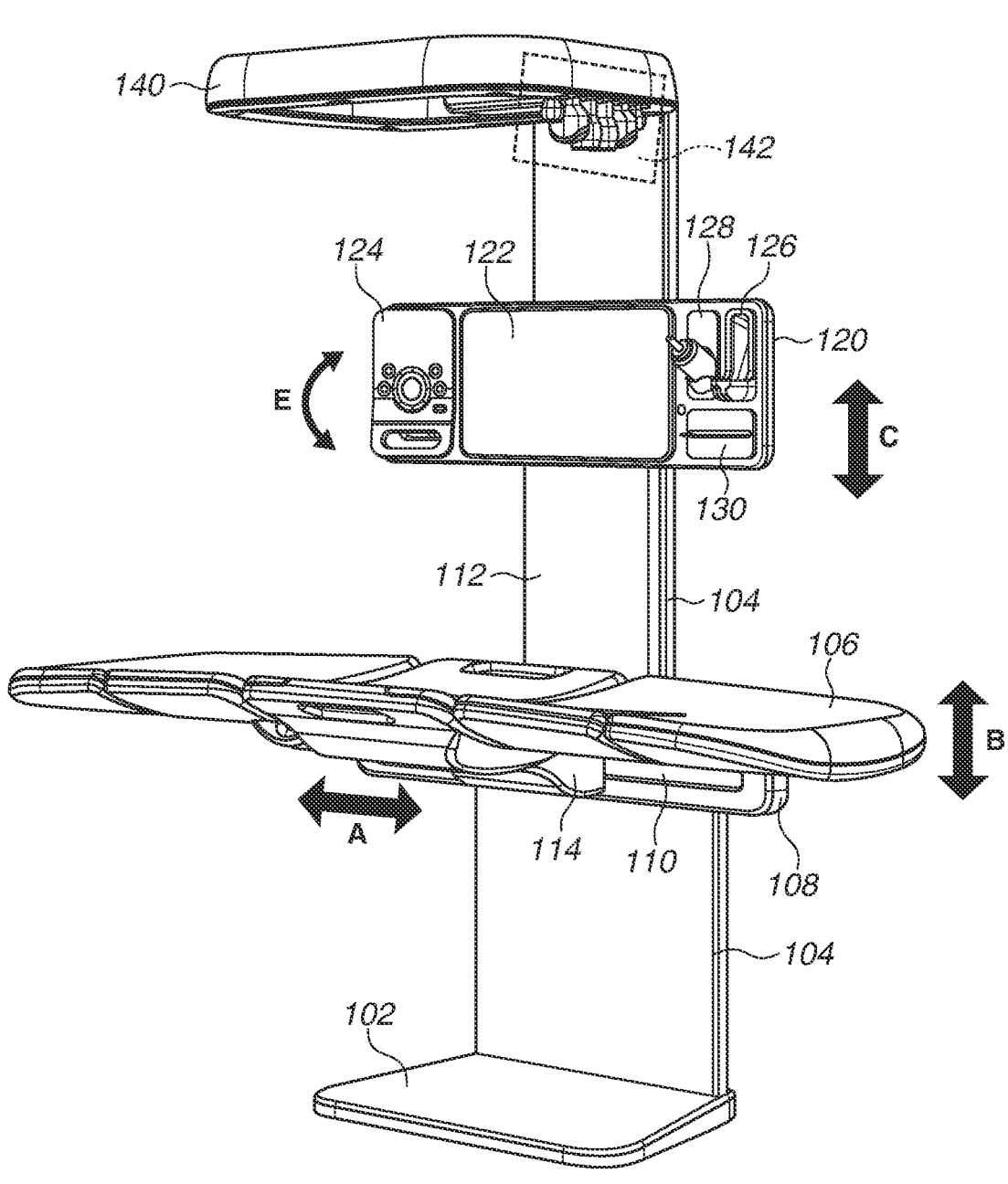
FIG. 3 is a perspective view illustrating a configuration of an ultrasonic diagnosis apparatus according to the present invention.

FIGS. 1 to 3 illustrate a configuration of the ultrasonic diagnosis apparatus according to the present invention. FIGS. 1 and 3 are perspective views of the ultrasonic diagnosis apparatus. FIG. 2 is a top view of the ultrasonic diagnosis apparatus.

A base portion 102 that supports the ultrasonic diagnosis apparatus relative to a floor surface is included. The base portion 102 is a member that has contact with the floor surface. The base portion 102 is fixed to the floor surface using a screw or the like. By releasing the base portion 102 fixed to the floor surface, an operator can move the ultrasonic diagnosis apparatus. In this example, a configuration in which the base portion 102 is installed on the floor surface is illustrated, but a configuration in which another base portion (not illustrated) is fixed to a ceiling, and the ultrasonic diagnosis apparatus is suspended from the ceiling may be employed.

The ultrasonic diagnosis apparatus includes a support unit 104 that is vertically installed on the floor surface or the ceiling, and supports each component of the ultrasonic diagnosis apparatus. The support unit 104 is integrated with the base portion 102. The support unit 104 is a member extending in an up-down direction (vertical direction), and can also be rephrased as a supporting column. The support unit 104 supports components of the ultrasonic diagnosis apparatus that are installed thereon in the up-down direction.

The ultrasonic diagnosis apparatus includes a bed unit 106 on which a subject is to be placed. The subject is to be placed on the top surface of the bed unit 106. The support unit 104 supports the bed unit 106 in such a manner that the top surface of the bed unit 106 becomes horizontal. The bed unit 106 is supported by the support unit 104 via a slide unit 108 installed on the support unit 104. A groove portion 110 is formed in the slide unit 108 in a horizontal direction. A bed support member 114 installed on the bottom surface of the bed unit 106 is fitted into the groove portion 110 of the slide unit 108. The bed support member 114 of the bed unit 106 is moved in the horizontal direction relative to the groove portion 110 of the slide unit 108, and whereby the bed unit 106 can slide in the horizontal direction (A direction) via the slide unit 108. The horizontal direction (A direction) is a longer direction of the bed unit 106.

In addition, the bed unit 106 is supported by the support unit 104 via a coupling unit 112 installed on the support unit 104. Because the coupling unit 112 is supported movably in the up-down direction relative to the support unit 104, the coupling unit 112 can move the bed unit 106 in the up-down direction (B direction). That is, the support unit 104 supports the bed unit 106 movably in the up-down direction. Because the support unit 104 supports the bed unit 106 to which load is applied, and a subject, the perimeter of the support unit 104 positioned inferior to the bed unit 106 is longer and thicker than the perimeter of the support unit 104 positioned superior to the bed unit 106. By varying the perimeter of the support unit 104 in this manner, the rigidity of the ultrasonic diagnosis apparatus is maintained.

The ultrasonic diagnosis apparatus includes a panel unit 120 including a plurality of components. The panel unit 120 includes a display unit 122 that displays an ultrasonic image generated by processing an ultrasonic signal, a measurement result, and the like. The display unit 122 is installed rotatably relative to the panel unit 120. By rotating the display unit 122, the operator can set the display unit 122 to a landscape-oriented state and a portrait-oriented state. The display unit 122 illustrated in FIG. 1 is in the landscape-oriented state. By rotating the display unit 122 by 90 degrees, the operator can set the display unit 122 to the portrait-oriented state. In accordance with the rotational angle of the display unit 122, the display unit 122 can also change the arrangement of an ultrasonic image and a measurement result.

The panel unit 120 includes an operation unit 124 to be operated by an operator. The panel unit 120 also includes an ultrasonic probe holder 126 for placing an ultrasonic probe, a bottle accommodation unit 128 that accommodates a bottle of ultrasound gel, and a box 130 of tissue paper for removing ultrasound gel adhering to a subject. The operation unit 124 is installed at one end (left side) of the panel unit 120. The ultrasonic probe holder 126, the bottle accommodation unit 128, and the box 130 of tissue paper are installed at another end (right side) of the panel unit 120. The panel unit 120 has a configuration in which the display unit 122 is installed among the operation unit 124, and the ultrasonic probe holder 126, the bottle accommodation unit 128, and the box 130 of tissue paper.

The ultrasonic probe holder 126 is a holding unit for tentatively placing an ultrasonic probe 144 being used in ultrasonic image capturing. The bottom surface of the ultrasonic probe holder 126 protrudes from the panel unit 120. The bottom surface of the ultrasonic probe holder 126 is a curved surface. The ultrasonic probe holder 126 can hold an ultrasonic wave transmission and reception surface (head portion) of the ultrasonic probe 144 on the bottom surface of the ultrasonic probe holder 126.

The bottle accommodation unit 128 has a function (gel warmer function) of warming the bottle of ultrasound gel. The bottle accommodation unit 128 can keep the bottle of ultrasound gel warm at a predetermined temperature (for example, 35 to 40° C.).

In this manner, the panel unit 120 can hold items necessary when the ultrasonic diagnosis apparatus is used. Thus, an operator can operate the operation unit of the ultrasonic diagnosis apparatus and acquire necessary items without changing a posture.

The panel unit 120 is coupled with the bed unit 106 via the coupling unit 112. The coupling unit 112 is installed along a longer direction of the support unit 104. A longer direction of the coupling unit 112 is parallel to the longer direction of the support unit 104. For example, a groove portion or a rail (not illustrated) is formed on the support unit 104 along the longer direction of the support unit 104. A part of the coupling unit 112 is fitted into the groove portion or the rail of the support unit 104, and the coupling unit 112 is installed on the support unit 104. Thus, even if load of the bed unit 106 or the like is applied to the coupling unit 112, the configuration as illustrated in FIG. 1 can be maintained.

In addition, the coupling unit 112 is installed movably in the up-down direction on the support unit 104. Because the coupling unit 112 can move in the up-down direction relative to the support unit 104, the coupling unit 112 can move the panel unit 120 in the up-down direction (C direction). The display unit 122 and the operation unit 124 installed on the panel unit 120 can move in the up-down direction via the coupling unit 112.

The operation unit 124 is installed on the panel unit 120 via an arm 132. The arm 132 has a structure in which a plurality of long cylindrical portions is incorporated into one another. That is, the arm 132 has a nesting structure, and is extendable and contractible in a longer direction (D direction) of the arm 132. By the extension and contraction of the arm 132, it is possible to change the position of the operation unit 124. In addition, the arm 132 is installed on the panel unit 120 via a hinge portion to be described below. Because the hinge portion serves as a pivot shaft of the arm 132, the hinge portion can swirl the arm 132 in a predetermined rotational direction (E direction). Thus, the operator can fold the arm 132 via the hinge portion. By folding the arm 132, the operator can accommodate the operation unit 124 in the panel unit 120.

Here, the configuration in which the display unit 122 and the operation unit 124 are supported by the support unit 104 via the panel unit 120 has been described, but the display unit 122 and the operation unit 124 may be directly supported by the support unit 104. In this case, the display unit 122 and the operation unit 124 each can move independently in the up-down direction.

The ultrasonic diagnosis apparatus includes a frame unit 140. The support unit 104 supports the frame unit 140. The frame unit 140 is supported at the uppermost part of the support unit 104. The frame unit 140 is a ring-shaped member having a hollow square shape with round corners. To reduce an oppressive feeling to a subject placed on the bed unit 106, a center portion of the frame unit 140 is a hollow. A plurality of ultrasonic probes 142 and 144 is installed on the frame unit 140. The frame unit 140 can also be rephrased as an accommodation unit of ultrasonic probes.

In addition, the accommodation unit of ultrasonic probes is installed on the frame unit 140 in such a manner that the ultrasonic probe 144 and the operation unit 124 do not interfere with (contact) each other when the ultrasonic probe 144 to be used in image capturing is drawn out (comes down) from the accommodation unit of cables of ultrasonic probes. Here, the description will be given assuming that the ultrasonic probe 144 is an ultrasonic probe to be used in image capturing but the same applies to the other ultrasonic probes 142. Specifically, the accommodation unit of ultrasonic probes is installed on the frame unit 140 on the right side when the ultrasonic diagnosis apparatus is viewed from the front. The ultrasonic probe 144 to be used in image capturing comes down from the frame unit 140 to the right side of the panel unit 120 (vicinity of the ultrasonic probe holder 126 and the bottle accommodation unit 128). In this manner, the accommodation unit of ultrasonic probes is installed immediately above the ultrasonic probe holder 126 and the bottle accommodation unit 128. Thus, because the ultrasonic probe 144 comes down from the frame unit 140 to the vicinity of the ultrasonic probe holder 126, the ultrasonic probe 144 can be tentatively placed on the ultrasonic probe holder 126.

On the other hand, the operation unit 124 is installed on the left side when the ultrasonic diagnosis apparatus is viewed from the front. Specifically, the operation unit 124 is installed on the left side of the panel unit 120. In this manner, the accommodation unit of ultrasonic probes is installed on the frame unit 140 not immediately above the operation unit 124. Thus, even if the ultrasonic probe 144 to be used in image capturing comes down from the frame unit 140, the ultrasonic probe 144 does not interfere with (contact) the operation unit 124.

As described above, the support unit 104 is vertically installed on the floor surface or the ceiling, and supports each component. In this example, the support unit 104 supports the bed unit 106, the operation unit 124, and the frame unit 140 (the accommodation unit of ultrasonic probes) in such a manner as to be separated in the up-down direction. In addition, the support unit 104 supports the bed unit 106, the display unit 122, and the frame unit 140 (the accommodation unit of ultrasonic probes) in such a manner as to be separated in the up-down direction. The support unit 104 supports the components separated into three areas corresponding to an upper part, a middle portion, and a lower portion, in such a manner as to be separated in the up-down direction.

The support unit 104 supports the components in such a manner that the components protrude toward one direction (forward direction in FIG. 1: direction orthogonal to the A direction and the B direction). The support unit 104 has a so-called cantilever structure, and supports the components in a state in which there is no external support other than the support unit 104. The bed unit 106, the operation unit 124, the display unit 122, and the frame unit 140 (the accommodation unit of ultrasonic probes) are installed on the support unit 104 in such a manner as to protrude toward one direction. If the bed unit 106, the operation unit 124 or the display unit 122, and the frame unit 140 (the accommodation unit of ultrasonic probes) are installed on the support unit 104 with being separated, the components become a layer structure.

Specifically, the bed unit 106 is supported at the lower portion of the support unit 104. The display unit 122 and the operation unit 124 are supported at the middle portion of the support unit 104. The frame unit 140 (the accommodation unit of ultrasonic probes) is supported at the upper part of the support unit 104. The display unit 122 is installed superior to the bed unit 106, and the operation unit 124 is installed superior to the bed unit 106. That is, the display unit 122 is installed at a position higher than a position at which the bed unit 106 is installed. In addition, the operation unit 124 is installed at a position higher than a position at which the bed unit 106 is installed.

The frame unit 140 is installed superior to the display unit 122, and the frame unit 140 is installed superior to the operation unit 124. That is, the frame unit 140 is installed at a position higher than a position at which the display unit 122 is installed. In addition, the frame unit 140 is installed at a position higher than a position at which the operation unit 124 is installed.

In addition, the frame unit 140 (the accommodation unit of ultrasonic probes) is installed immediately above the bed unit 106. Thus, in a case where the plurality of ultrasonic probes 142 and 144 is lowered from the frame unit 140, the ultrasonic probes are arranged onto the bed unit 106.

Because the display unit 122 is installed superior to the bed unit 106, an operator can check the state of a subject placed on the bed unit 106 and a contact point of the ultrasonic probe 144 being used in image capturing of the subject, and also observe an ultrasonic image, a measurement result, and the like that are displayed on the display unit 122. In addition, because the operation unit 124 is installed superior to the bed unit 106, an operator can check the state of the subject and an installation point of the ultrasonic probe 144 being used in image capturing, and also operate the operation unit 124. In the ultrasonic diagnosis apparatus according to the present invention, the operator is assumed to operate the operation unit 124 while standing near the center in the longer direction of the bed unit 106. Thus, the components including the display unit 122, the operation unit 124, the ultrasonic probe 144, and the bed unit 106 can be installed in front of the operator. The operator can therefore perform image capturing in a natural posture without twisting the operator's body.

Because the support unit 104 supports the components in such a manner that the components protrude toward one direction (forward direction in FIG. 1: direction orthogonal to the A direction and the B direction), no component protrudes from the rear surface of the support unit 104 (toward a direction opposite to the one direction (backward direction in FIG. 1)). Thus, the operator can bring the rear surface of the support unit 104 closer to a wall surface of an inspection room, and install the ultrasonic diagnosis apparatus near the wall surface of the inspection room. Because the ultrasonic diagnosis apparatus can be installed on the wall side of the inspection room, a space of the inspection room can be ensured.

FIG. 2 is a top view of the ultrasonic diagnosis apparatus. The details of the bed unit 106 and the operation unit 124 of the ultrasonic diagnosis apparatus will be described with reference to FIG. 2.

The bed unit 106 broadly includes three frames. Specifically, the bed unit 106 includes a first frame 450 that supports a low back of a subject, a second frame 452 that supports an upper body of the subject, and a third frame 454 that supports a lower body of the subject.

The first frame 450 includes grip portions 400 and 402 to be gripped by a subject or an operator. When a subject gets onto the bed unit 106, the subject grips at least one of the grip portions 400 and 402. The subject can support the subject's body using the grip portions 400 and 402. The subject moves while gripping the grip portions 400 and 402 in such a manner that the low back of the subject is positioned at the first frame 450. The subject is placed near the center of the bed unit 106. The subject may grip the grip portions 400 and 402 with both hands. When the subject gets onto the bed unit 106 or gets off from the bed unit 106, the operation unit 124 is accommodated in the panel unit 120.

In addition, in a case where an operator desires to slide the bed unit 106 in the horizontal direction (the A direction), the operator grips the grip portion 400 and pulls the bed unit 106 in a direction in which the bed unit 106 is desired to be slid. The operator can slide the bed unit 106 in the horizontal direction. By the grip portions 400 and 402 being installed on the bed unit 106, the operability of the bed unit 106 improves.

The first frame 450 is fixedly installed on the bed support member 114 illustrated in FIG. 1. The bed support member 114 supports the first frame 450 in such a manner that the first frame 450 keeps a horizontal state. The first frame 450 and the second frame 452 are partitioned across a partition groove 420. A tilt shaft is installed in the partition groove 420. An end portion of the first frame 450 and an end portion of the second frame 452 are coupled to the tilt shaft. The first frame 450 and the second frame 452 have a structure of bending at the tilt shaft installed in the partition groove 420. The second frame 452 rotates around the tilt shaft to tilt in such a manner that an angle formed by the first frame 450 and the second frame 452 becomes a minor angle (angle smaller than 180 degrees). At this time, the first frame 450 keeps a horizontal state without rotating around the tilt shaft. By rotating the second frame 452 to tilt, it is possible to recline the bed unit 106.

In a similar manner, the first frame 450 and the third frame 454 are partitioned across a partition groove 422. A tilt shaft is installed in the partition groove 422. An end portion of the first frame 450 and an end portion of the third frame 454 are coupled to the tilt shaft. The first frame 450 and the third frame 454 have a structure of bending at the tilt shaft installed in the partition groove 422. The third frame 454 can be rotated around the tilt shaft to tilt in such a manner that an angle formed by the first frame 450 and the third frame 454 becomes a major angle (angle larger than 180 degrees). At this time, the first frame 450 keeps a horizontal state without rotating around the tilt shaft. By rotating the third frame 454 to tilt, it is possible to recline the bed unit 106.

In the bed unit 106, a plurality of grooves (groove 404, groove 406, groove 408) is respectively formed in the first frame 450, the second frame 452, and the third frame 454. The bed unit 106 can be separated by the plurality of grooves. A member of the first frame 450 in which the grip portion 400 is positioned can be separated by the groove 404. By separating the member of the first frame 450 in which the grip portion 400 is positioned, it is possible to form the bed unit 106 into a U shape. Similarly, a member of the second frame 452 that is surrounded by the groove 408 and a member of the third frame 454 that is surrounded by the groove 406 are separated. It is possible to separate a part of a member of the second frame 452 and a part of a member of the third frame 454.

The operation unit 124 is installed on the panel unit 120 via the arm 132. The arm 132 is installed on the panel unit 120 via a hinge portion 134 (first hinge portion). The hinge portion 134 is a torque hinge, for example. The torque hinge is a hinge that can stop the arm 132 opening or closing, at an arbitrary position. The torque hinge has a rotation torque that can support the weights of the arm 132 and the operation unit 124. The torque hinge can adjust the rotation torque using an adjustment screw (not illustrated). In this manner, the arm 132 can be swirled to a predetermined angle using the hinge portion 134. Thus, as illustrated in FIG. 2, the operation unit 124 can be extended out, and the operation unit 124 can be installed above (immediately above) the bed unit 106.

Even if a subject is placed on the bed unit 106, by swirling the arm 132 up to a predetermined angle at which the operation unit 124 does not contact the subject, it is possible to extend the operation unit 124 out. For example, the predetermined angle can be set to 120 degrees. It is possible to swirl the arm 132 in such a manner that an angle formed by the panel unit 120 and the arm 132 falls within the range of 0 degree to 120 degrees.

FIG. 3 is a perspective view of the ultrasonic diagnosis apparatus. An accommodation configuration of the operation unit 124 of the ultrasonic diagnosis apparatus will be described with reference to FIG. 3.

As illustrated in FIGS. 1 and 2, by swirling the arm 132 that supports the operation unit 124, it is possible to fold the arm 132. Specifically, as described above, the hinge portion 134 is installed between the panel unit 120 and the arm 132. A hinge portion (second hinge portion: not illustrated) is installed also between the operation unit 124 and the arm 132. The operation unit 124 is installed on the arm 132 via the hinge portion. Specifically, the hinge portion is installed on the back surface of the operation unit 124. Because the function of the hinge portion (second hinge portion) is similar to that of the hinge portion 134 (first hinge portion), the description will be omitted.

In this manner, the arm 132 is installed on the panel unit 120 via the hinge portion 134 (first hinge portion). In addition, the operation unit 124 is installed on the arm 132 via the hinge portion (second hinge portion). As illustrated in FIG. 3, it is possible to fold the arm 132 via the two hinge portions installed at both ends of the arm. At this time, the arm 132 enters a state of being sandwiched between the panel unit 120 and the operation unit 124. In this manner, it is possible to accommodate the operation unit 124 in the panel unit 120. If the operation unit 124 is accommodated in the panel unit 120, an operation surface of the operation unit 124 faces front. Because the operation surface of the operation unit 124 faces front, even in a state in which the operation unit 124 is accommodated as illustrated in FIG. 3, an operator can operate the operation unit 124 and perform image capturing using the ultrasonic diagnosis apparatus.

Figure 4:
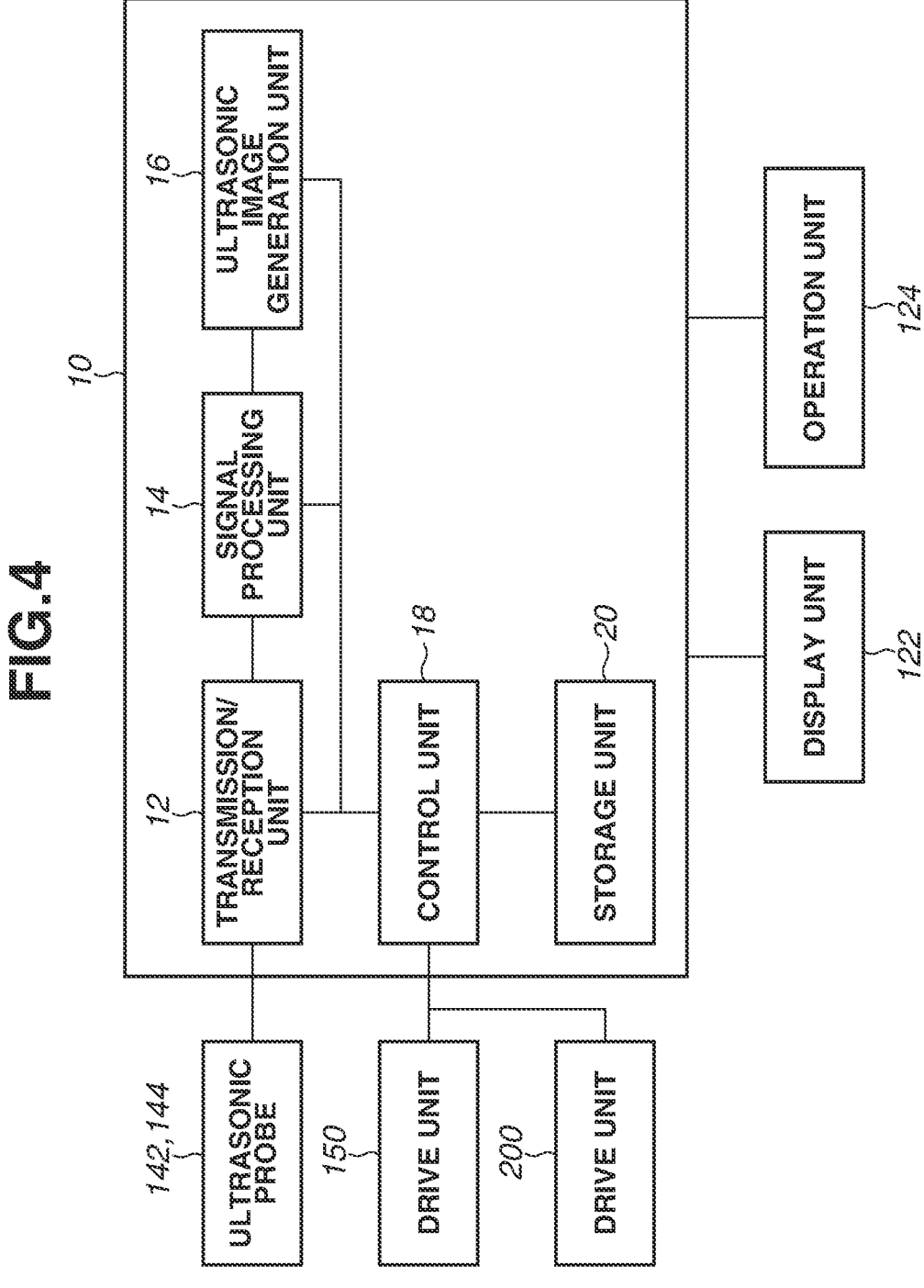
FIG. 4 is a diagram illustrating a configuration of an apparatus main body in an ultrasonic diagnosis apparatus according to the present invention.

Here, an internal configuration of the ultrasonic diagnosis apparatus will be described with reference to FIG. 4. FIG. 4 is a diagram illustrating an apparatus main body 10 of the ultrasonic diagnosis apparatus. The apparatus main body 10 is installed inside the support unit 104 or inside the panel unit 120, for example. The apparatus main body 10 may be installed at any location in the ultrasonic diagnosis apparatus.

The apparatus main body 10 includes a transmission/reception unit 12 that transmits and receives ultrasonic waves to and from the ultrasonic probes 142 and 144, a signal processing unit 14 that performs various types of signal processing using an ultrasonic signal that is based on a reflected wave signal received by the transmission/reception unit 12, an ultrasonic image generation unit 16 that generates an ultrasonic image using signal processing data signal-processed by the signal processing unit 14, and a control unit 18 that controls various components. The control unit 18 controls a drive unit 150 for moving the plurality of ultrasonic probes 142 and 144 in the up-down direction, and a drive unit 200 for moving the panel unit 120 (the display unit 122 and the operation unit 124) and the bed unit 106 in the up-down direction, which will be described below.

In this example, the ultrasonic probe 144 is regarded as an ultrasonic probe to be used in image capturing. The transmission/reception unit 12 controls transmission and reception of ultrasonic waves that are performed by the ultrasonic probe 144. The transmission/reception unit 12 includes a transmission unit, a transmission delay circuit, and the like, and supplies a drive signal to the ultrasonic probe 144. The transmission unit repeatedly generates a rate pulse at a predetermined repetition frequency (pulse repetition frequency: PRF). In addition, the transmission delay circuit converges ultrasonic waves generated from the ultrasonic probe 144, and gives a delay time to determine transmission directional characteristics, to the rate pulse generated by the transmission unit. By changing the delay time to be given to the rate pulse, the transmission delay circuit can control a transmission direction of ultrasonic waves to be transmitted from an oscillator.

In addition, the transmission/reception unit 12 includes an amplifier, an analog/digital (A/D) conversion unit, a reception delay circuit, an addition circuit, and the like. An ultrasonic signal is generated by various types of processing on a reflected wave signal received by the ultrasonic probe 144. The amplifier performs gain correction processing by amplifying the reflected wave signal for each channel. The A/D conversion unit performs A/D conversion of the gain-corrected reflected wave signal. The reception delay circuit gives a delay time to digital data to determine reception directional characteristics. The addition circuit performs addition processing of the reflected wave signal to which the delay time is given by the reception delay circuit. By the addition processing performed by the addition circuit, a reflection component from the direction corresponding to the reception directional characteristics of the reflected wave signal is emphasized.

In the case of two-dimensionally scanning a subject, the transmission/reception unit 12 causes a two-dimensional ultrasonic wave to be transmitted from the ultrasonic probe 144. Then, the transmission/reception unit 12 generates a two-dimensional ultrasonic signal from a two-dimensional reflected wave signal received by the ultrasonic probe 144. In addition, in the case of three-dimensionally scanning a subject, the transmission/reception unit 12 causes a three-dimensional ultrasonic wave to be transmitted from the ultrasonic probe 144. Then, the transmission/reception unit 12 generates a three-dimensional ultrasonic signal from a three-dimensional reflected wave signal received by the ultrasonic probe 144.

The signal processing unit 14 performs various types of signal processing on an ultrasonic signal output from the transmission/reception unit 12. Specifically, the signal processing unit 14 performs signal processing such as detection processing and logarithmic compression on the ultrasonic signal. The signal processing unit 14 generates signal processing data (raster data) by imaging amplitude information of the ultrasonic signal. The signal processing unit 14 performs bandpass filter processing on the ultrasonic signal output from the transmission/reception unit 12, and then detects an envelope curve of the output signal. Then, the signal processing unit 14 performs compression processing on the detected data by logarithmic conversion. The signal processing unit 14 outputs signal processing data obtained after the signal processing, to the ultrasonic image generation unit 16.

The ultrasonic image generation unit 16 generates an ultrasonic image using the signal processing data signal-processed by the signal processing unit 14. The ultrasonic image generation unit 16 includes a digital scan converter, and converts the signal processing data into data represented by orthogonal coordinates. In this example, the ultrasonic image generation unit 16 orthogonal-transforms the signal processing data (raster data) into a coordinate system (X, Y) of image data for display. Then, the ultrasonic image generation unit 16 generates an ultrasonic image (B mode image data) in which a signal intensity is represented by the brightness of luminance. In this manner, the generation of an ultrasonic image is performed by the ultrasonic image generation unit 16. As a generation algorithm of an ultrasonic image, it is possible to perform image reconstruction by applying an arbitrary algorithm aside from phasing addition processing.

In addition, the ultrasonic image generation unit 16 can generate blood flow image data using a color Doppler method called a color flow mapping method (CFM). In the color Doppler method, by performing frequency analysis that is based on a Doppler effect, from a reflected wave signal received by transmitting ultrasonic waves in the same one direction a plurality of times, it is possible to extract kinetic information of a blood flow. Using the color Doppler method, the ultrasonic image generation unit 16 generates blood flow information such as an average speed, variance, and power, as blood flow image data. The ultrasonic image generation unit 16 may generate blood flow image data using a power Doppler method.

The operation unit 124 includes a plurality of input components, and inputs at least information regarding ultrasonic waves. The information regarding ultrasonic waves is information regarding the transmission of ultrasonic waves, the stop of ultrasonic waves, the depth of ultrasonic waves, the repetition frequency of ultrasonic waves, the measurement of ultrasonic waves, and the like, for example. The plurality of input components includes a keyboard, a trackball, and various buttons. The operation unit 124 receives various instructions from an operator, and transmits the received various instruction to the control unit 18 of the apparatus main body 10. For example, a measurement caliper moves on an ultrasonic image in accordance with the motion of the trackball or the like of the operation unit 124. The operator performs position adjustment in such a manner that the measurement caliper falls within a measurement range of a measurement portion. Then, by pressing a determination button, the operator can acquire the size (for example, distance, perimeter, or area) of the measurement range.

The display unit 122 displays a graphical user interface (GUI) for an operator inputting various instructions using the operation unit 124, and displays an ultrasonic image, blood flow image data, a measurement result, and the like that have been generated in the apparatus main body 10.

The plurality of ultrasonic probes 142 and 144 is connected to the apparatus main body 10. The plurality of ultrasonic probes 142 and 144 each includes a plurality of oscillators, and can generate ultrasonic waves by driving the plurality of oscillators. The plurality of ultrasonic probes 142 and 144 receives a reflected wave from a subject and convert the reflected wave into an electronic signal. The converted electronic signal is transmitted to the apparatus main body 10.

In addition, the plurality of ultrasonic probes 142 and 144 each includes an acoustic matching layer that is provided on the foreside (subject side) of the plurality of oscillators, and matches acoustic impedances of the plurality of oscillators and the subject, and a backing material that is provided on the back surface side of the plurality of oscillators, and prevents the propagation of ultrasonic waves from the plurality of oscillators to the back surface side.

The plurality of ultrasonic probes 142 and 144 is detachably connected to the frame unit 140 (the accommodation unit of ultrasonic probes). The types of the ultrasonic probes include a linear type, a sector type, a convex type, a radial type, and a three-dimensional scanning type, and an operator can select the types of the ultrasonic probes in accordance with the purpose of image capturing. In addition, the type of a sensor to be applied to an ultrasonic probe is not limited to a conventional sensor that uses a bulk piezoelectric zirconate titanate (PZT). It is possible to use a capacitance type probe of a type called a capacitive micromachined ultrasonic transducer (CMUT) that uses a fine processing technique, or a probe of a type called a piezoelectric micromachined ultrasonic transducer (PMUT) combined also with a piezoelectric thin film technique.

FIGS. 5 to 7B are diagrams illustrating vertical driving of a component in the ultrasonic diagnosis apparatus according to the present invention.

Figure 5:
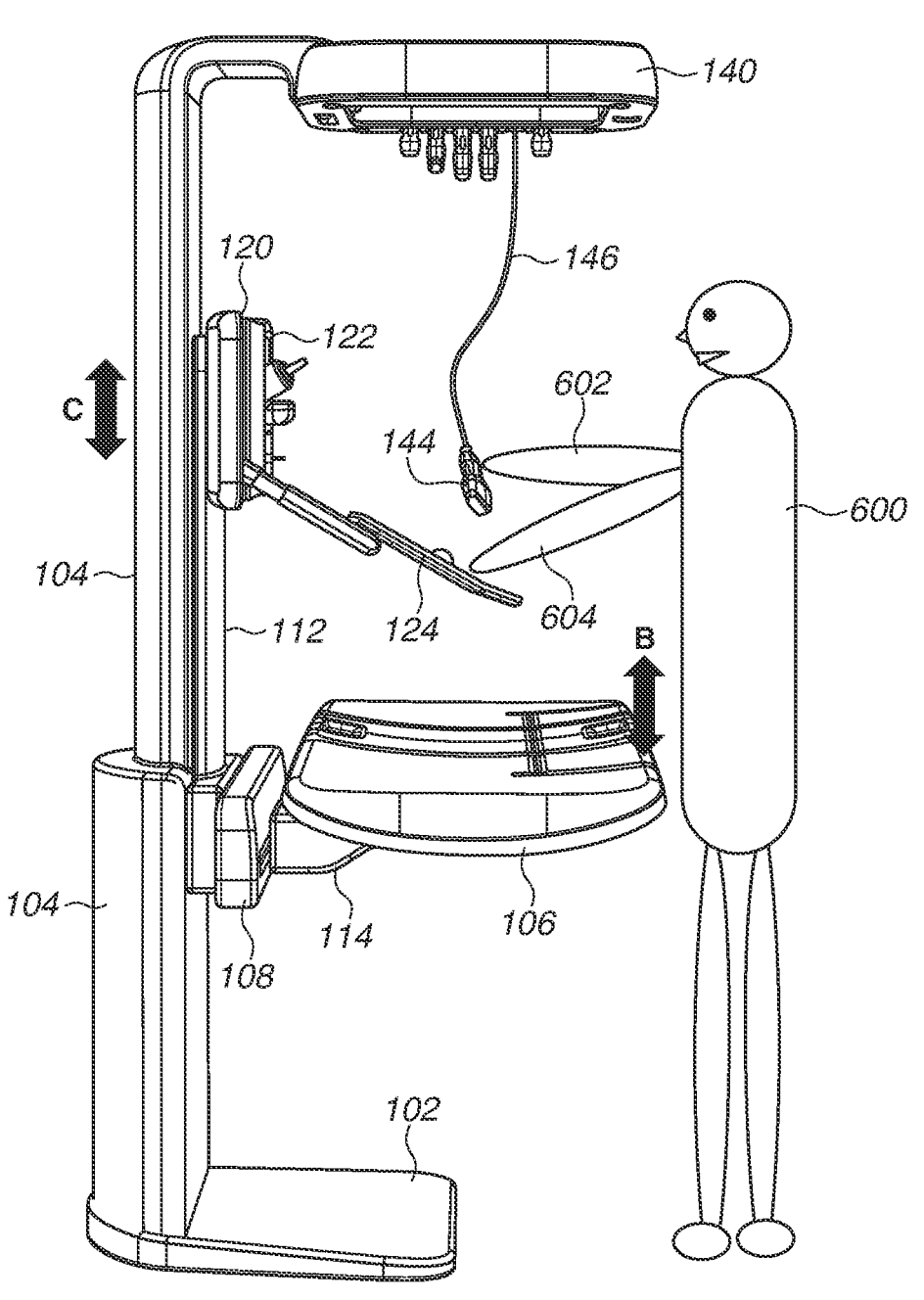
FIG. 5 is a diagram illustrating vertical driving of a component in an ultrasonic diagnosis apparatus according to the present invention.

FIG. 5 illustrates a configuration in which an operator 600 captures an image of a subject in a standing state. The operator 600 is assumed to perform an operation with standing near the center in the longer direction of the bed unit 106. The operator captures an image of a subject (not illustrated) placed on the bed unit 106, using the ultrasonic probe 144 that has come down from the frame unit 140 (the accommodation unit of ultrasonic probes) and the operation unit 124. The ultrasonic probe 144 can transmit and receive ultrasonic waves based on an electronic signal transmitted from a cable 146. At this time, a right hand 602 of the operator 600 grips the ultrasonic probe 144 and a left hand 604 of the operator 600 operates the operation unit 124.

In this manner, the display unit 122, the operation unit 124, the ultrasonic probe 144, and the bed unit 106 can be installed in front of the operator 600. Thus, the operator 600 can perform image capturing in a natural posture with facing the ultrasonic diagnosis apparatus and the subject.

The operator 600 can install the display unit 122 at an arbitrary position. Because the coupling unit 112 can move in the up-down direction relative to the support unit 104, the operator 600 can move the panel unit 120 in the up-down direction. The display unit 122 installed on the panel unit 120 can move in the up-down direction (C direction). It is therefore possible to set the display unit 122 at the same height as the height of eyes of the operator.

The control unit 18 of the ultrasonic diagnosis apparatus can also automatically control the heights of the display unit 122 and the operation unit 124 in accordance with body shape information of the operator 600. The ultrasonic diagnosis apparatus includes a sensor (not illustrated) that reads body shape information (body length, etc.) of the operator 600. The body shape information of the operator 600 that has been output from the sensor is transmitted to the control unit 18. The control unit 18 controls the drive unit 200 (vertical drive unit) to be described below, based on the body shape information of the operator, and adjusts the heights of the display unit 122 and the operation unit 124. Specifically, the control unit 18 adjusts the heights of the display unit 122 and the operation unit 124 in such a manner that an upper end of the display unit 122 is set at the height equivalent to the body length of the operator 600, or the position of the operation unit 124 is set at the height corresponding to the low back of the operator 600. It is therefore possible to ease a bowing posture of the operator 600.

In addition, the control unit 18 of the ultrasonic diagnosis apparatus can also automatically control the heights of the display unit 122 and the operation unit 124 in accordance with prestored body shape information of the operator 600. A storage unit 20 can store body shape information of the operator 600, and the operator 600 prestores the body shape information into the storage unit 20. For example, the operator 600 stores a body length, a line-of-sight position, and the like of the operator 600 into the storage unit 20.

When the operator 600 operates the ultrasonic diagnosis apparatus, the body shape information of the operator 600 is transmitted from the storage unit 20 to the control unit 18. Based on the body shape information of the operator 600, the control unit 18 controls the drive unit 200 (vertical drive unit), and adjusts the heights of the display unit 122 and the operation unit 124. Specifically, the control unit 18 adjusts the heights of the display unit 122 and the operation unit 124 in such a manner that an upper end of the display unit 122 is set at the height equivalent to the body length of the operator 600. Alternatively, the control unit 18 can also adjust the heights of the display unit 122 and the operation unit 124 in such a manner that a screen of the display unit 122 is set at the height corresponding to the line-of-sight of the operator 600 (for example, in such a manner that a line-of-sight direction becomes equal to the horizontal direction).

Furthermore, the control unit 18 of the ultrasonic diagnosis apparatus can also automatically control the heights of the display unit 122 and the operation unit 124 based on setting information set for each operator. The storage unit 20 can store setting information (for example, the heights of the display unit 122 and the operation unit 124) set by a plurality of operators, and each piece of setting information is stored into the storage unit 20. Here, in a case where the operator 600 operates the ultrasonic diagnosis apparatus, a state in which the operator 600 is operating the operation unit 124 is acquired from login information of the ultrasonic diagnosis apparatus and transmitted to the control unit 18. Based on the login information of the operator 600, setting information of the operator 600 is transmitted from the storage unit 20 to the control unit 18. Based on the setting information of the operator 600, the control unit 18 controls the drive unit 200 (vertical drive unit) and adjusts the heights of the display unit 122 and the operation unit 124. In a case where a different operator operates the ultrasonic diagnosis apparatus, the control unit 18 controls the drive unit 200 (vertical drive unit) and adjusts the heights of the display unit 122 and the operation unit 124, based on setting information of the different operator.

In addition, the operator 600 can install the bed unit 106 at an arbitrary position. Because the coupling unit 112 can move in the up-down direction relative to the support unit 104, the bed unit 106 can be moved in the up-down direction (B direction).

The panel unit 120 is coupled with the bed unit 106 via the coupling unit 112, and a distance between the panel unit 120 and the bed unit 106 is kept constant. The distance between the panel unit 120 and the bed unit 106 can be arbitrarily adjusted in accordance with the body length of the operator 600 and the intended use. For example, the operator can adjust the distance between the panel unit 120 and the bed unit 106 within the range from 50 cm to 100 cm.

If the operator moves the display unit 122 installed on the panel unit 120, in the up-down direction, the bed unit 106 moves in the up-down direction in accordance with the movement of the display unit 122. In a similar manner, if the operator moves the operation unit 124 installed on the panel unit 120, in the up-down direction, the bed unit 106 also moves in the up-down direction in accordance with the movement of the operation unit 124.

In other words, the display unit 122 and the bed unit 106 are supported by the support unit 104 in such a manner that the display unit 122 and the bed unit 106 move in the up-down direction in a mutually-interlocked manner. The display unit 122 and the bed unit 106 move in an interlocked manner in a state in which a constant distance is kept between the display unit 122 and the bed unit 106. In addition, the operation unit 124 and the bed unit 106 are supported by the support unit 104 in such a manner that the operation unit 124 and the bed unit 106 move in the up-down direction in a mutually-interlocked manner. The operation unit 124 and the bed unit 106 move in an interlocked manner in a state in which a constant distance is kept between the operation unit 124 and the bed unit 106.

That is, the support unit 104 is installed on the floor surface or the ceiling, and virtually-movably supports the operation unit 124 and the bed unit 106. The support unit 104 virtually-movably supports the display unit 122 and the bed unit 106. The display unit 122 and the bed unit 106 do not move in an interlocked manner in the horizontal direction. In a similar manner, the operation unit 124 and the bed unit 106 do not move in an interlocked manner in the horizontal direction.

Figure 6:
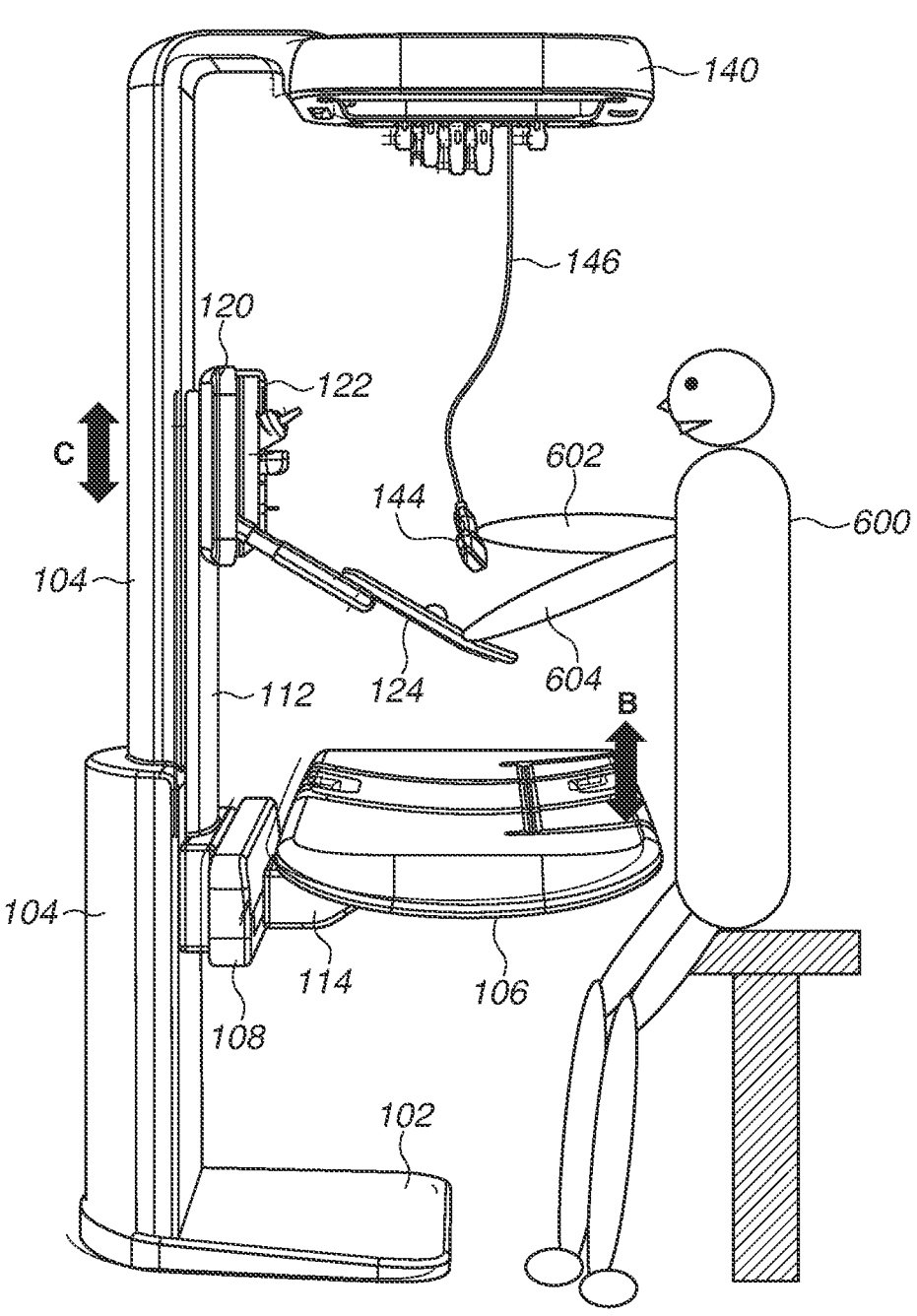
FIG. 6 is a diagram illustrating vertical driving of a component in an ultrasonic diagnosis apparatus according to the present invention.

FIG. 6 illustrates a configuration in which the operator 600 captures an image of a subject in a seated state. The operator 600 is assumed to perform an operation with being seated on a chair 210 near the center in the longer direction of the bed unit 106.

If the coupling unit 112 is moved in a lower direction and the panel unit 120 (the display unit 122 and the operation unit 124) and the bed unit 106 are moved in the lower direction from the configuration of the ultrasonic diagnosis apparatus that is illustrated in FIG. 5, the configuration of the ultrasonic diagnosis apparatus that is illustrated in FIG. 6 is obtained. In the configuration of the ultrasonic diagnosis apparatus that is illustrated in FIG. 6, as compared with the configuration of the ultrasonic diagnosis apparatus that is illustrated in FIG. 5, a distance between the bed unit 106 and the floor surface becomes closer, and a distance between the bed unit 106 and the frame unit 140 becomes farther.

The operator 600 captures an image of a subject (not illustrated) placed on the bed unit 106, using the ultrasonic probe 144 that has come down from the frame unit 140 (the accommodation unit of ultrasonic probes) and the operation unit 124. Because the operator can place the operator's knees under the bed unit 106, it is possible to avoid a twist posture of the low back.

In this manner, even in a state in which the operator 600 is seated on the chair 210, the display unit 122, the operation unit 124, the ultrasonic probe 144, and the bed unit 106 can be installed in front of the operator. Thus, the operator 600 can perform image capturing in a natural posture with facing the subject.

Figure 7A:
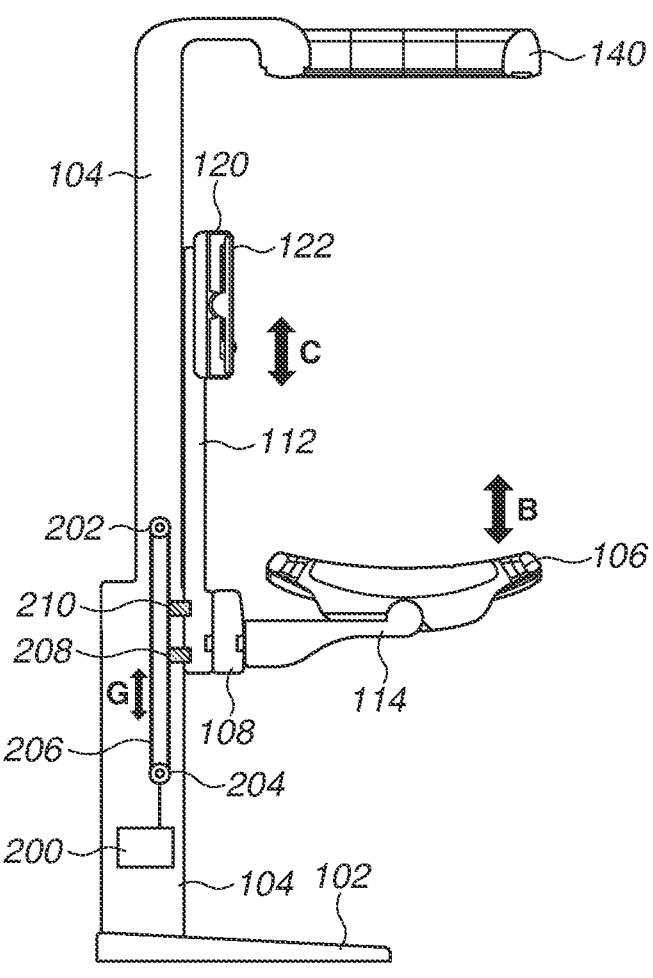
FIG. 7A is a diagram illustrating vertical driving of a component in an ultrasonic diagnosis apparatus according to the present invention.
Figure 7B:
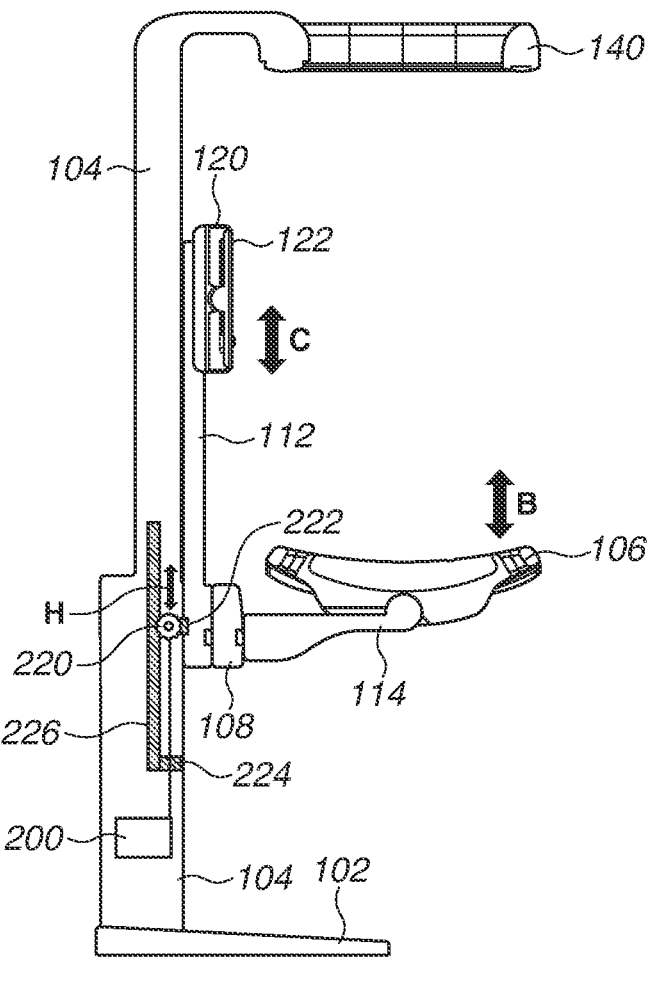
FIG. 7B is a diagram illustrating vertical driving of a component in an ultrasonic diagnosis apparatus according to the present invention.

The vertical driving of a component in the ultrasonic diagnosis apparatus will be described with reference to FIGS. 7A and 7B. FIGS. 7A and 7B are longitudinal sectional views of the ultrasonic diagnosis apparatus. The longitudinal sectional views of the ultrasonic diagnosis apparatus are longitudinal sectional views taken along a center line (dashed-dotted line) extending in the up-down direction in FIG. 2.

FIG. 7A illustrates a configuration of a vertical drive unit (belt type) that moves components such as the bed unit 106 and the panel unit 120 (the display unit 122, the operation unit 124) in the up-down direction.

The inside of the support unit 104 is hollow. Pulleys 202 and 204 (a plurality of pulleys) and a belt 206 are installed inside the support unit 104. The pulleys 202 and 204 are rotators. The pulleys 202 and 204 are installed with being separated in the longer direction of the support unit 104. A tilt shaft of the pulley 202 and a rotating shaft of the pulley 204 are installed on an inner wall of the support unit 104, and rotatably support the pulleys 202 and 204. A rotating shaft of the pulley 202 and the rotating shaft of the pulley 204 are parallel to a horizontal surface. The belt 206 is stretched around the pulleys 202 and 204 (a plurality of pulleys) in a tensioned state. The belt 206 is desirably a belt made of material that is less likely to cause slippage, or a gear belt. The pulleys 202 and 204 have a function of transmitting power to the belt 206.

If either one of the pulleys 202 and 204 is rotated, the belt 206 slides in the up-down direction (G direction).

Belt fixing portions 208 and 210 are installed on the front surface of the belt 206. The belt fixing portion portions 208 and 210 are fixedly installed on the belt 206 and the coupling unit 112. The belt fixing portion portions 208 and 210 and the coupling unit 112 are integrated. The belt 206 and the coupling unit 112 are thereby integrated.

In addition, the coupling unit 112 is integrated with the bed unit 106 via the slide unit 108. The coupling unit 112 is integrated with the panel unit 120 (the display unit 122, the operation unit 124). Thus, the belt 206 is integrated with the bed unit 106 and the panel unit 120 (the display unit 122, the operation unit 124).

If either one of the pulleys 202 and 204 is rotated and force is added to the belt 206 by the motor driving of the drive unit 200 in the vertical drive unit, the belt 206 slides in the up-down direction (G direction), and the coupling unit 112 can be moved in the up-down direction. By moving the coupling unit 112 in the up-down direction, it is possible to move components such as the bed unit 106 and the panel unit 120 (the display unit 122, the operation unit 124) in the up-down direction (the B direction, the C direction).

Specifically, if the pulley 204 is rotated counterclockwise and the belt 206 in contact with the pulley 204 is rotated counterclockwise by the motor driving of the drive unit 200, the belt fixing portions 208 and 210 move in the upper direction. If the belt fixing portions 208 and 210 move in the upper direction, it is possible to move the coupling unit 112 in the upper direction, and move components such as the bed unit 106 and the panel unit 120 (the display unit 122, the operation unit 124) in the upper direction.

If the pulley 204 is rotated clockwise and the belt 206 in contact with the pulley 204 is rotated clockwise by the motor driving of the drive unit 200, the belt fixing portions 208 and 210 move in the lower direction. If the belt fixing portions 208 and 210 move in the lower direction, it is possible to move the coupling unit 112 in the lower direction, and move components such as the bed unit 106 and the panel unit 120 (the display unit 122, the operation unit 124) in the lower direction.

A distance between the pulleys 202 and 204 is longer than a stroke width in the up-down direction in components such as the bed unit 106 and the panel unit 120 (the display unit 122, the operation unit 124). A slide width of the belt 206 is equivalent to the stroke width in the up-down direction in components such as the bed unit 106 and the panel unit 120 (the display unit 122, the operation unit 124). If the belt 206 tries to slide by a width exceeding the slide width, the slide of the belt unit 206 is locked by the control unit 18.

In this manner, the vertical drive unit (belt type) that moves the coupling unit 112 in the up-down direction is included inside the support unit 104. In accordance with the movement in the up-down direction of the coupling unit 112, components such as the bed unit 106 and the panel unit 120 (the display unit 122, the operation unit 124) can be moved in the up-down direction.

FIG. 7B illustrates a configuration (rack and pinion type) of a vertical drive unit that vertically moves components such as the bed unit 106 and the panel unit 120 (the display unit 122, the operation unit 124). The inside of the support unit 104 is hollow. A circular gear 220 and a gear support unit 222 that rotatably supports the circular gear 220 are installed inside the support unit 104. The gear support unit 222 is fixedly installed on the coupling unit 112, and the gear support unit 222 and the coupling unit 112 are integrated.

In addition, the coupling unit 112 is integrated with the bed unit 106 via the slide unit 108. The coupling unit 112 is integrated with the panel unit 120 (the display unit 122, the operation unit 124). Thus, the circular gear 220 and the gear support unit 222 are integrated with the bed unit 106 and the panel unit 120 (the display unit 122, the operation unit 124).

The gear support unit 222 supports the circular gear 220 in such a manner that a rotating shaft of the circular gear 220 becomes parallel to the horizontal surface. The circular gear 220 can be rotated by motor driving. The drive unit 200 that rotates the circular gear 220 by motor driving is included inside the support unit 104.

In addition, a plate-like rod member 226 and a rod member support unit 224 that supports the rod member 226 are installed inside the support unit 104. The rod member support unit 224 is inscribed in the support unit 104, and the rod member support unit 224 is fixedly installed on the support unit 104. The plate-like rod member 226 is installed along the longer direction of the support unit 104 (the up-down direction). The longer direction of the support unit 104 is a direction orthogonal to the horizontal surface.

The surface of the rod member 226 has a protruding and recessed shape fitting with a gear shape of the circular gear 220.

The circular gear 220 and the rod member 226 engage with each other. If rotational force is added to the circular gear 220 by the drive unit 200, the circular gear 220 rolls on the surface of the rod member 226, and the coupling unit 112 can be moved in the up-down direction (H direction). That is, the circular gear 220 can be moved in the up-down direction by the drive unit 200. By moving the coupling unit 112 in the up-down direction, it is possible to move components such as the bed unit 106 and the panel unit 120 (the display unit 122, the operation unit 124) in the up-down direction (the B direction, the C direction).

Specifically, if the circular gear 220 is rotated clockwise by the drive unit 200 in the vertical drive unit, the circular gear 220 rolls on the rod member 226 along a longer direction of the rod member 226, and moves in the lower direction. If the circular gear 220 moves in the lower direction, the coupling unit 112 can be moved in the lower direction, and components such as the bed unit 106 and the panel unit 120 (the display unit 122, the operation unit 124) can be moved in the lower direction.

On the other hand, if the circular gear 220 is rotated counterclockwise by the drive unit 200, the circular gear 220 rolls on the rod member 226 along the longer direction of the rod member 226, and moves in the upper direction. If the circular gear 220 moves in the upper direction, the coupling unit 112 can be moved in the upper direction, and components such as the bed unit 106 and the panel unit 120 (the display unit 122, the operation unit 124) can be moved in the upper direction.

As the method of vertical driving in the present invention, examples of the belt type and the rack and pinion type have been described above, but another configuration such as a gear type or a combination of a cam follower and a guide rail may be employed.

Figure 8:
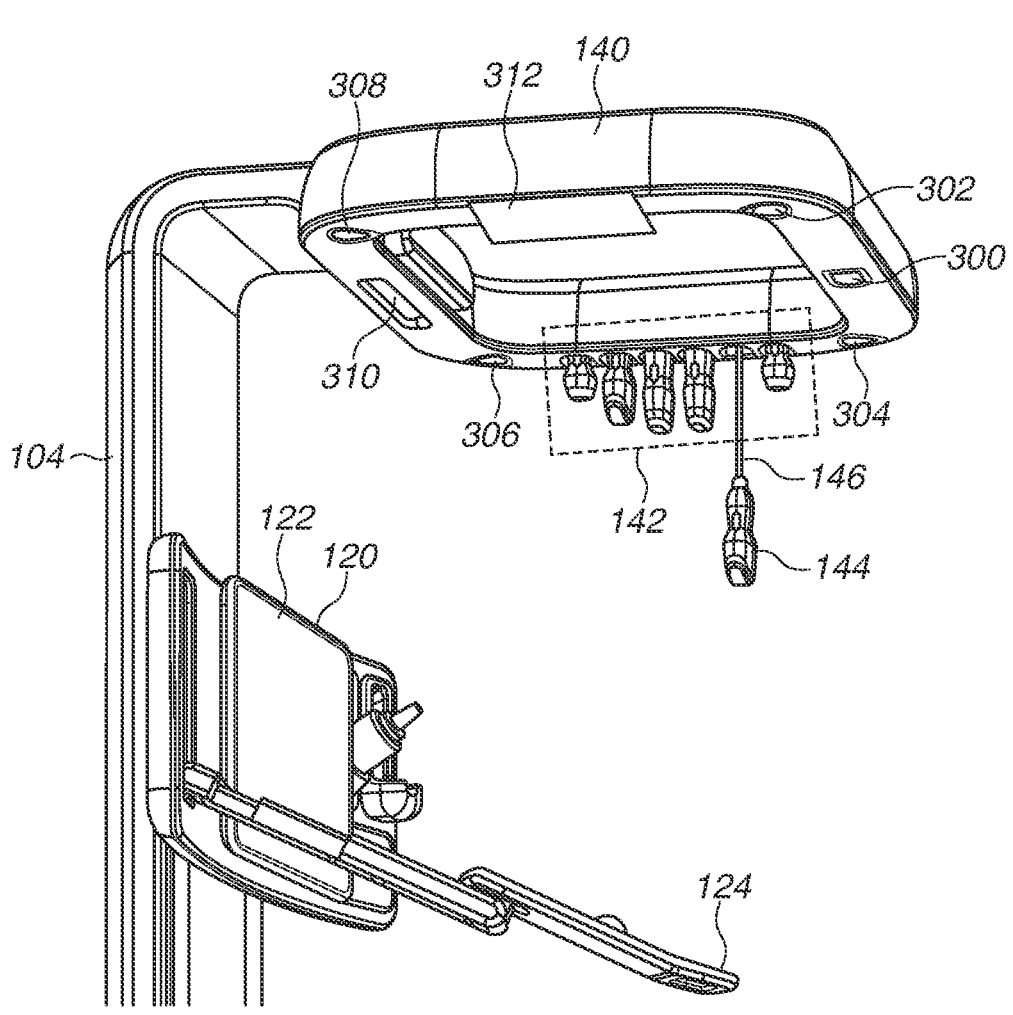
FIG. 8 is a diagram illustrating a configuration of a frame unit in an ultrasonic diagnosis apparatus according to the present invention.
Figure 9:
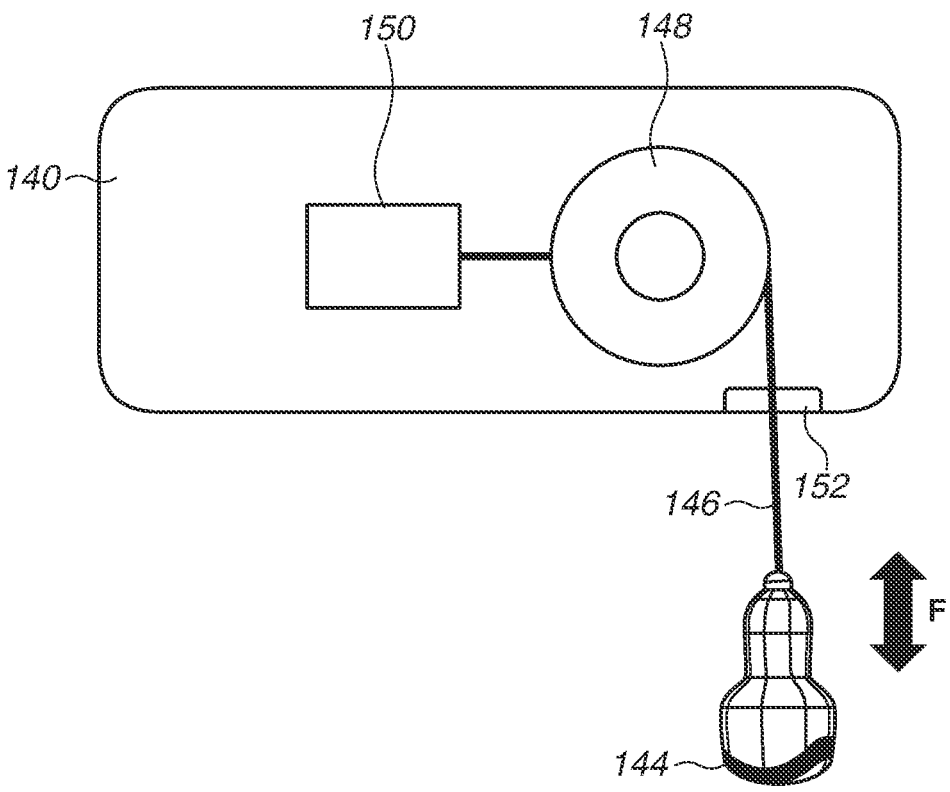
FIG. 9 is a diagram illustrating a configuration of a frame unit in an ultrasonic diagnosis apparatus according to the present invention.

FIGS. 8 and 9 are diagrams illustrating a configuration of the frame unit 140 in the ultrasonic diagnosis apparatus according to the present invention.

As illustrated in FIG. 8, the support unit 104 supports the frame unit 140 at the uppermost part. The frame unit 140 does not move in the up-down direction. The frame unit 140 accommodates the ultrasonic probes 142 and 144. Aside from the accommodation unit of ultrasonic probes, the frame unit 140 includes an emergency stop button 300, projection units 302 and 304, cameras 306 and 308, and a sensor 310.

The emergency stop button 300 is a button for stopping an operation of a component of the ultrasonic diagnosis apparatus. When components such as the bed unit 106 and the panel unit 120 (the display unit 122, the operation unit 124) are moving in the up-down direction using the drive unit 200, in some cases, there is a danger that a subject placed on the bed unit 106 and a component (for example, the display unit 122, the operation unit 124) of the ultrasonic diagnosis apparatus have contact.

At this time, by the operator pressing the emergency stop button 300, an operation of the component of the ultrasonic diagnosis apparatus is stopped. Specifically, the emergency stop button 300 is connected to the control unit 18. In a case where the emergency stop button 300 has been pressed, a notification (stop signal) indicating that the emergency stop button 300 has been pressed is transmitted to the control unit 18. The control unit 18 stops motor driving of the drive unit 200, and stops the movement in the up-down direction of the coupling unit 112. Thus, the movement of components such as the bed unit 106 and the panel unit 120 (the display unit 122, the operation unit 124) is stopped.

In this manner, a danger that a subject and a component of the ultrasonic diagnosis apparatus have contact is avoided using the emergency stop button 300.

As an example of stopping an operation of a component of the ultrasonic diagnosis apparatus, the control of the drive unit 200 has been described. Alternatively, by the operator pressing the emergency stop button 300, the control unit 18 may stop transmission and reception of ultrasonic waves in the ultrasonic probe 144.

The frame unit 140 includes the cameras 306 and 308 that mainly capture images of a subject placed on the bed unit 106. The control unit 18 can display images captured by the cameras 306 and 308, on the display unit 122. The cameras 306 and 308 may be depth cameras that acquire depth information (up-down direction) of a subject placed on the bed unit 106.

The cameras 306 and 308 are arranged in parallel. By the control unit 18 performing image processing on images acquired from the two cameras, it is possible to measure depth information of the subject. For example, in a stereo camera system, depth information of the subject is measured from parallax information of the cameras 306 and 308. In a Time of Flight (ToF) camera system, by emitting near infrared rays onto a subject from either one of the cameras 306 and 308, and measuring a time until a reflected wave reflected from the subject reaches, depth information of the subject is measured. The control unit 18 can acquire three-dimensional information including depth information of the subject, using the cameras 306 and 308. By recognizing depth information of the subject, the control unit 18 can set a drawing amount (length) of the cable 146 of the ultrasonic probe 144 to be used in image capturing.

In addition, by a recognition technique of cameras, the control unit 18 can acquire various types of information of the subject. For example, the control unit 18 can acquire a body size of the subject, the position of an organ that the ultrasonic probe 144 contacts (image capturing region), and the like. The control unit 18 can also associate an ultrasonic image generated by the ultrasonic image generation unit 16, depth information of the subject, the body size of the subject, and an image capturing region. The storage unit 20 can store the ultrasonic image, the depth information of the subject, the body size of the subject, and the image capturing region in association with each other.

The projection units 302 and 304 project a projected image onto the bed unit 106 or a subject placed on the bed unit 106.

The projection units 302 and 304 include a light source lamp, a lens, and the like, for example. The projection units 302 and 304 separate colors of the light source lamp into red, green, and blue, which are light's three primary colors. Then, the projection units 302 and 304 generate images of the respective colors on a transmissive panel, and project the images from the lens.

Images projected from the projection units 302 and 304 can include position information of the ultrasonic probe 144 of which the image has been captured last. Specifically, the cameras 306 and 308 are connected to the control unit 18. The cameras 306 and 308 capture images of the ultrasonic probe 144 brought into contact with the subject, and the control unit 18 analyzes the images acquired from the cameras 306 and 308. The control unit 18 acquires position information of the ultrasonic probe 144 from the analyzed images. The storage unit 20 stores the position information of the ultrasonic probe 144. The projection units 302 and 304 acquire the position information of the ultrasonic probe 144 that is stored in the storage unit 20, and project the position information of the ultrasonic probe 144 onto a subject placed on the bed unit 106. By checking, from the projected image, the position information of the ultrasonic probe 144 of which the image has been captured last, the operator can perform image capturing while bringing the ultrasonic probe 144 into contact with the same position. Accordingly, the operator can check a temporal change based on the last and current ultrasonic image data.

The two projection units corresponding to the projection units 302 and 304 are installed on the frame unit 140. By combining images projected from the projection units 302 and 304, it is possible to display, in a larger size, an image projected on the bed unit 106 or a subject placed on the bed unit 106.

In addition, items to be projected from the projection units 302 and 304 can be made different. For example, it is also possible to project an image from one projection unit and project a descriptive text from the other projection unit.

The projection units 302 and 304 can also function as an illumination unit that illuminates the bed unit 106. In some cases, an inspection room where the ultrasonic diagnosis apparatus is installed is dark and it is difficult for a subject to recognize an ultrasonic diagnosis apparatus. By the projection units 302 and 304 illuminating the bed unit 106, a subject can easily recognize the ultrasonic diagnosis apparatus. In addition, by the projection units 302 and 304 illuminating the bed unit 106, the floor surface near the ultrasonic diagnosis apparatus becomes brighter. It is therefore possible to lead to the prevention of stumbling of an operator or a subject.

It is also possible to set illumination light by combining red, green, and blue in the light source lamp of the projection units 302 and 304. In addition, the projection units 302 and 304 can also have a function of narrowing an exposure field in such a manner that illumination light does not enter the face of the subject.

The sensor 310 is a human detection sensor, for example, and can detect the presence or absence of an operator near the ultrasonic diagnosis apparatus and the presence or absence of a subject placed on the bed unit 106. The sensor 310 and the control unit 18 are connected, and presence or absence information of an operator or a subject is transmitted to the control unit 18. In accordance with the presence or absence of an operator or a subject, the control unit 18 can perform various types of control. For example, in a case where an operator gets closer to the ultrasonic diagnosis apparatus and the subject, the control unit 18 activates the projection units 302 and 304 as the illumination unit. In addition, in a case where a subject is placed on the bed unit 106, the control unit 18 restricts the vertical movement of the above-described vertical drive unit.

As illustrated in FIG. 8, the accommodation unit that accommodates the plurality of ultrasonic probes 142 and 144 is installed on the frame unit 140. The accommodation unit in the frame unit 140 that accommodates ultrasonic probes is installed superior to the bed unit 106. That is, the accommodation unit that accommodates ultrasonic probes is installed at a position higher than a position at which the bed unit 106 is installed. In addition, the accommodation unit that accommodates ultrasonic probes is installed superior to the operation unit 124 or the display unit 122. That is, the accommodation unit that accommodates ultrasonic probes is installed at a position higher than a position at which the operation unit 124 or the display unit 122 is installed.

The plurality of ultrasonic probes 142 and 144 is installed side by side on the frame unit 140 and accommodated therein. The plurality of ultrasonic probes 142 and 144 is installed side by side in a direction parallel to a shorter direction of the bed unit 106, and accommodated therein. The plurality of ultrasonic probes 142 and 144 is accommodated with being arranged at equal intervals in such a manner as not to contact each other. Because the plurality of ultrasonic probes 142 and 144 is installed side by side on one side of the frame unit 140, even if the ultrasonic probe 144 to be used in image capturing is lowered from the frame unit 140, cables of the respective ultrasonic probes do not get tangled. In addition, because the ultrasonic probe 144 is in a state of being suspended from the frame unit 140, the cable 146 of the ultrasonic probe 144 is installed superior to the ultrasonic probe 144. That is, the cable 146 is installed at a position higher than a position at which the ultrasonic probe 144 is installed. While the ultrasonic probe 144 contacts a subject, the cable 146 never contacts the subject unless the cable 146 installed superior to the ultrasonic probe 144 warps. Thus, the cable 146 can keep a hygienic state.

FIG. 9 is a diagram illustrating a longitudinal section of the frame unit 140, and is a diagram illustrating a configuration of the accommodation unit of ultrasonic probes. FIG. 9 illustrates an accommodation configuration of the ultrasonic probe 144, but an accommodation configuration of the plurality of other ultrasonic probes 142 is similar to this.

As illustrated in FIG. 9, a hole portion 152 is formed on the bottom surface of the frame unit 140. The cable 146 of the ultrasonic probe 144 is arranged in the hole portion 152. The frame unit 140 includes a winding unit 148 that winds up the cable 146 of the ultrasonic probe 144, and the drive unit 150 that drives the winding unit 148.

The cable 146 is winded around the winding unit 148. A rotating shaft of the winding unit 148 is installed on an inner wall of the frame unit 140, and rotatably supports the winding unit 148. The rotating shaft of the winding unit 148 is parallel to the horizontal surface.

By the motor driving of the drive unit 150, it is possible to rotate the winding unit 148 and move the cable 146 in the up-down direction (F direction). Thus, the ultrasonic probe 144 can be moved in the up-down direction.

If the drive unit 150 rotates the winding unit 148 clockwise, the cable 146 is drawn out, and the ultrasonic probe 144 can be lowered in the lower direction. The operator can perform image capturing using the ultrasonic probe 144 lowered in the lower direction.

A draw-out rotation amount (clockwise) of the winding unit 148 is equivalent to a length by which the cable 146 is drawn out. A rotation amount of the winding unit 148 may be preset in the drive unit 150. The control unit 18 can preset a draw-out rotation amount (clockwise) of the winding unit 148 in the drive unit 150 in such a manner that a length of the cable 146 from the frame unit 140 becomes a predetermined length (for example, 100 cm).

If the drive unit 150 rotates the winding unit 148 counterclockwise, the cable 146 is drawn back, and the ultrasonic probe 144 can be moved in the upper direction. A draw-back rotation amount (counterclockwise) of the winding unit 148 is equivalent to the draw-out rotation amount (clockwise) of the winding unit 148.

In this manner, the operator can accommodate the ultrasonic probe 144.

The operator can select an ultrasonic probe to be used in image capturing, from among the plurality of ultrasonic probes 142 accommodated in the frame unit 140 (the accommodation unit of ultrasonic probes). If an ultrasonic probe to be used in image capturing is selected by the operator, the control unit 18 controls the drive unit 150 rotate the winding unit 148 corresponding to the selected ultrasonic probe 144, clockwise. The selected ultrasonic probe 144 comes down from the frame unit 140.

The control unit 18 may make a setting in such a manner that the ultrasonic probe 144 that is suitable for an inspection region of a subject or satisfies an image capturing condition is selected, and comes down from the frame unit 140. In a case where an image of a desired region (first region) in a subject is to be captured, the control unit 18 controls the drive unit 150 that performs the vertical movement of an ultrasonic probe that can perform image capturing of the desired region (first region). In a case where an image of a desired region (second region) in a subject is to be captured, the control unit 18 controls the drive unit 150 that performs the vertical movement of an ultrasonic probe that can perform image capturing of the desired region (second region). In addition, in a case where image capturing of a subject is performed under a desired image capturing condition (first image capturing condition), the control unit 18 controls the drive unit 150 that performs the vertical movement of an ultrasonic probe that can perform image capturing under the desired image capturing condition (first image capturing condition). In addition, in a case where image capturing of a subject is performed under a desired image capturing condition (second image capturing condition), the control unit 18 controls the drive unit 150 that performs the vertical movement of an ultrasonic probe that can perform image capturing under the desired image capturing condition (second image capturing condition).

For example, in a case where an image of a carotid artery of a subject is to be captured, the control unit 18 controls the drive unit 150 that performs vertical movement of a linear-type ultrasonic probe, to rotate the winding unit 148 clockwise. In this manner, a cable of the linear-type ultrasonic probe is drawn out, and the linear-type ultrasonic probe comes down from the frame unit 140. At this time, it is also possible to notify an operator that the linear-type ultrasonic probe has been selected, by lighting an illumination unit (light-emitting diode (LED)) installed inside the linear-type ultrasonic probe.

In a case where an image of an abdominal part of a subject is to be captured, the control unit 18 controls the drive unit 150 that performs vertical movement of a convex-type ultrasonic probe, to rotate the winding unit 148 clockwise. In this manner, a cable of the convex-type ultrasonic probe is drawn out, and the convex-type ultrasonic probe comes down from the frame unit 140. At this time, it is also possible to notify an operator that the convex-type ultrasonic probe has been selected, by lighting an illumination unit (LED) installed inside the convex-type ultrasonic probe.

In a case where an image of a heart of a subject is to be captured, the control unit 18 controls the drive unit 150 that performs vertical movement of a sector-type ultrasonic probe, to rotate the winding unit 148 clockwise. In this manner, a cable of the sector-type ultrasonic probe is drawn out, and the sector-type ultrasonic probe comes down from the frame unit 140. At this time, it is also possible to notify an operator that the sector-type ultrasonic probe has been selected, by lighting an illumination unit (LED) installed inside the sector-type ultrasonic probe.

The ultrasonic probe 144 that has come down from the frame unit 140 may perform ultrasonic wave transmission and reception in such a manner that an image of a subject can be promptly captured. The operator can capture an image of a subject placed on the bed unit 106, using the ultrasonic probe 144 that has come down from the frame unit 140.

The winding unit 148 may use a spiral spring (not illustrated) installed inside the winding unit 148. If the cable 146 is drawn out, a drum rotates and the spiral spring is winded up. The ultrasonic probe 144 and the cable 146 enter a state of being drawn out from the frame unit 140.

The spiral spring has a property of returning to an original state. The cable 146 returns to the hole portion 152 and is winded up by the winding unit 148, but by a brake (not illustrated), the rotation of the drum is prevented and the cable 146 is prevented from returning. In a state in which the ultrasonic probe 144 and the cable 146 are drawn out from the frame unit 140, the operator performs image capturing of a subject using the ultrasonic probe 144.

After the image of the subject has been captured, the operator releases the brake. If the brake is released, the spiral spring tries to return to the original state and the drum rotates, and the cable 146 is winded up. In this manner, the ultrasonic probe 144 and the cable 146 are accommodated in the frame unit 140.

In addition, in a case where a desired ultrasonic probe is not included in the plurality of ultrasonic probes 142 accommodated in the frame unit 140 (the accommodation unit of ultrasonic probes), an ultrasonic probe can also be replaced. Specifically, a connector portion (not illustrated) is installed at an end portion of the cable 146, and the ultrasonic probe 144 and the cable 146 can be separated off.

The connector portion is a member for connecting the ultrasonic probe 144 to the ultrasonic diagnosis apparatus. The connector portion includes a terminal that engages with the ultrasonic probe 144. By the ultrasonic probe 144 and the cable 146 being connected by the connector portion, it is possible to connect the ultrasonic probe 144 and the transmission/reception unit 12 in the apparatus main body 10. In addition, by a different ultrasonic probe and the cable 146 being connected by the connector portion, it is possible to connect the different ultrasonic probe and the transmission/reception unit 12 in the apparatus main body 10.

Here, the ultrasonic probe 144 and the cable 146 have been described, but other ultrasonic probes and cables also have a similar configuration. In this manner, by replacing an ultrasonic probe, it is possible to install various ultrasonic probes such as a radial-type probe or an endoscope probe not illustrated in FIG. 8.

The plurality of ultrasonic probes 142 and 144 includes cables, but the plurality of ultrasonic probes 142 and 144 may be wireless ultrasonic probes. The wireless ultrasonic probe includes a wireless transmission unit, a wireless receiving unit, a battery, and the like. By the wireless transmission unit and the wireless receiving unit, wireless communication between the wireless ultrasonic probe and the apparatus main body 10 can be performed.

In addition, it is possible to fit the wireless ultrasonic probe into the hole portion 152 of the frame unit 140.

In addition, the frame unit 140 has a function of charging the battery of the wireless ultrasonic probe.

In addition, a display unit 312 that displays an ultrasonic image may be installed on the frame unit 140. The display unit 312 is detachably attached to the frame unit 140. The display unit 312 is connected with the apparatus main body 10. The display unit 312 can display an ultrasonic image generated by the ultrasonic image generation unit 16. A display surface of the display unit 312 faces downward, and faces toward the side of a subject placed on the bed unit 106. The subject can view the display unit 312 while lying on the back with the face up. That is, the subject can view the display unit 312 in a natural state without changing a posture. The subject can check a disease state, the state of a pre-born child, and the like from ultrasonic image data. The operator can explain a disease state, the state of a pre-born child, and the like with the subject being placed on the bed unit 106.

Figure 10:
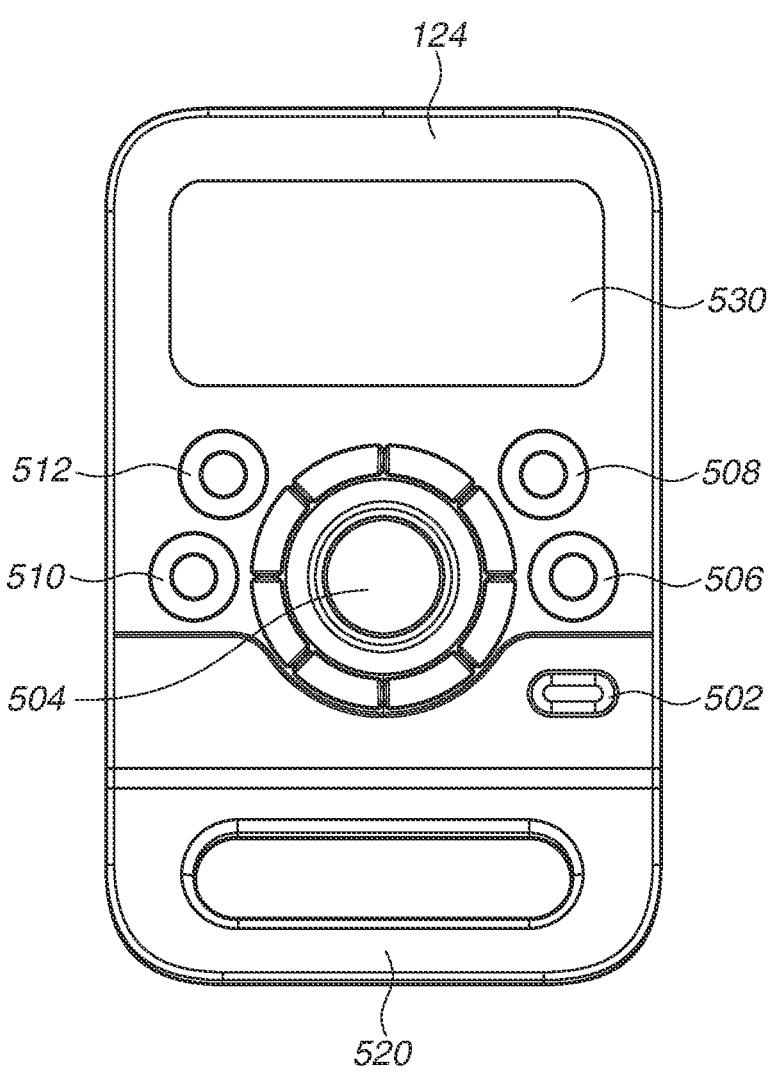
FIG. 10 is a diagram illustrating a configuration of an operation unit in an ultrasonic diagnosis apparatus according to the present invention.

FIG. 10 is a diagram illustrating a configuration of the operation unit 124 in the ultrasonic diagnosis apparatus according to the present invention.

The operation unit 124 includes a freeze button 502 for freezing an ultrasonic image displayed on the display unit 122. The freeze button 502 of the operation unit 124 is a button for freezing (stopping) when an ultrasonic image displayed in real time is to be stored. If the operator presses the freeze button 502 in a state in which the ultrasonic probe 144 is not moved, an ultrasonic image displayed in real time on the display unit 122 can be frozen. The data of the frozen ultrasonic image can be stored into the storage unit 20.

The operation unit 124 includes a trackball 504. By an operator operating the trackball 504, it is possible to move a measurement caliper and move various commands.

The operation unit 124 includes switches 506 to 510 circularly-arranged around the trackball 504. The switches 506 to 510 include a B mode switch for selecting a B mode as an ultrasonic image capturing method, a CFM mode switch for selecting a CFM mode, a Doppler mode switch for selecting a Doppler mode, an M mode switch for selecting an M mode, and the like. If a button is selected from among the switches 506 to 510, the selected button is illuminated with an LED or the like. The operator can recognize that the button has been selected.

The operation unit 124 includes a handle 520 to be gripped by an operator. The operator can move the operation unit 124 while gripping the handle 520. For example, the operation unit 124 can be drawn out from the panel unit 120 as illustrated in FIG. 1, or the operation unit 124 can be accommodated in the panel unit 120 as illustrated in FIG. 3.

An inclination is formed in the handle 520 in the upper direction relative to the surface of an upper part of the operation unit 124, and the handle 520 also has a function of a palm rest. The operator can operate the freeze button 502, the trackball 504, and the switches 506 to 510 while placing the operator's palm on the handle 520.

The operation unit 124 includes a screen 530. A mode selected using the switches 506 to 510, information regarding a subject, and the like are displayed on the screen 530.

Figure 11:
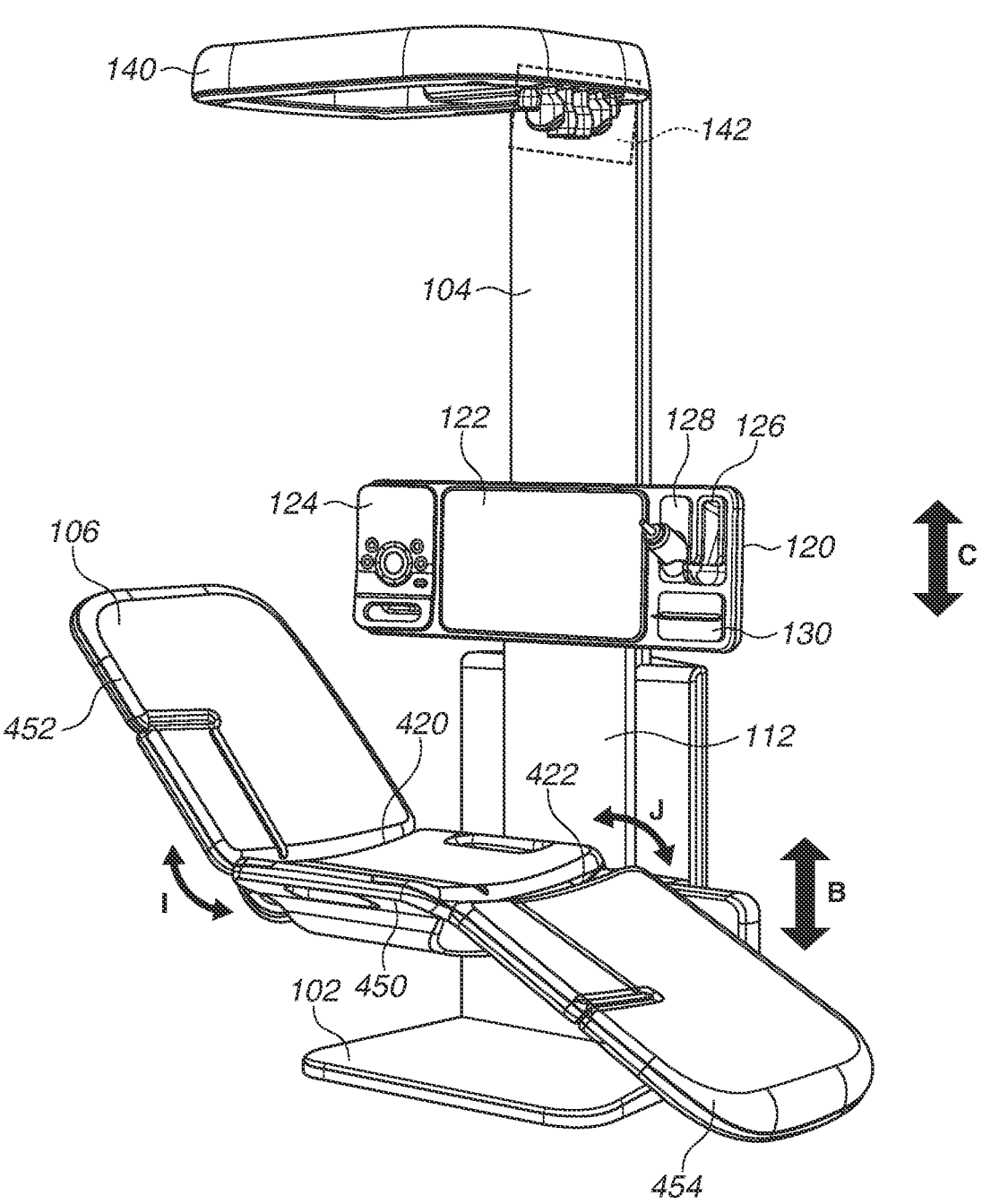
FIG. 11 is a diagram illustrating a modified example of a bed unit in an ultrasonic diagnosis apparatus according to the present invention.
Figure 12:
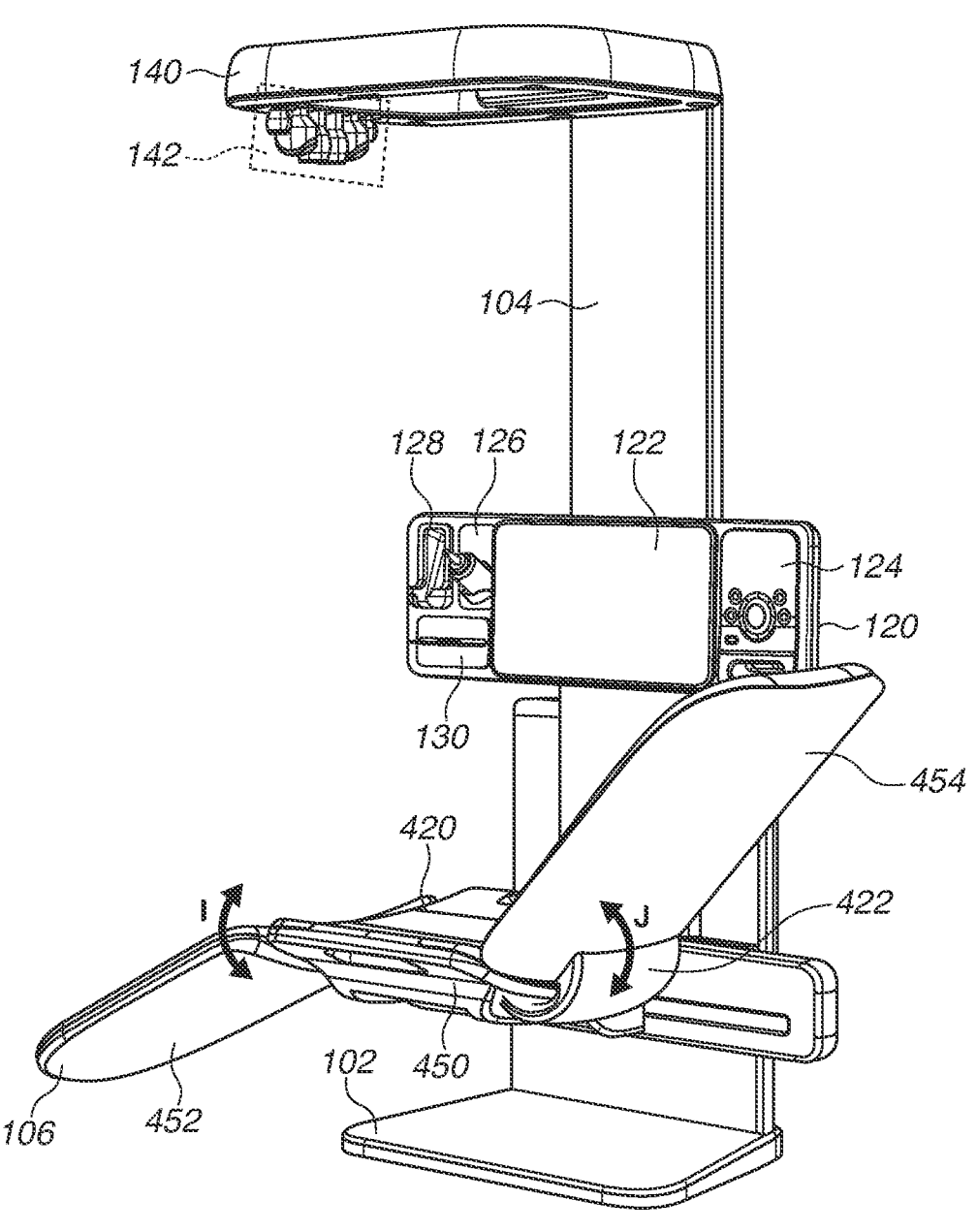
FIG. 12 is a diagram illustrating a modified example of components (bed unit, operation unit, etc.) in an ultrasonic diagnosis apparatus according to the present invention.

FIGS. 11 and 12 are diagrams each illustrating a modified example of the bed unit 106 in the ultrasonic diagnosis apparatus according to the present invention.

As illustrated in FIG. 11, the bed unit 106 include a first frame 450 that supports a low back of a subject, a second frame 452 that supports an upper body of the subject, and a third frame 454 that supports a lower body of the subject.

A tilt shaft is installed between the first frame 450 and the second frame 452. In other words, the tilt shaft is installed in the partition groove 420. The tilt shaft between the first frame 450 and the second frame 452 is parallel to the horizontal surface, and parallel to the shorter direction of the bed unit 106.

A drive unit is installed inside the bed unit 106 (the partition groove 420). By the motor driving of the drive unit, the second frame 452 can be rotated around the tilt shaft in a predetermined rotational direction (I direction). The operator can rotate the second frame 452 and tilt the second frame 452 upward. By tilting the second frame 452 upward, it is possible to straighten up the upper body of the subject.

A tilt shaft is installed between the first frame 450 and the third frame 454. In other words, the tilt shaft is installed in the partition groove 422. The tilt shaft between the first frame 450 and the third frame 454 is parallel to the horizontal surface, and parallel to the shorter direction of the bed unit 106.

A drive unit is installed inside the bed unit 106 (the partition groove 422). By the motor driving of the drive unit, the third frame 454 can be rotated around the tilt shaft in a predetermined rotational direction (J direction). The operator can rotate the third frame 454 around the tilt shaft and tilt the third frame 454 downward. By tilting the third frame 454 downward, it is possible to lower the lower body of the subject.

As illustrated in FIG. 11, the bed unit 106 can be reclined, and has a shape like a chair. The operator can capture an image of a subject using an ultrasonic probe in a state in which the bed unit 106 is reclined.

In addition, as illustrated in FIG. 11, in a state in which the bed unit 106 is reclined (state in which a backrest is provided), the subject can get onto the bed unit 106. Then, it is also possible to change the state from the state of the ultrasonic diagnosis apparatus that is illustrated in FIG. 11, to the state of the ultrasonic diagnosis apparatus that is illustrated in FIG. 1, and bring the bed unit 106 into a horizontal state. Specifically, the operator brings the second frame 452 into the horizontal state by rotating the second frame 452, and brings the third frame 454 into the horizontal state by rotating the third frame 454. In this manner, the bed unit 106 can be brought into horizontal state, and the operator can capture an image of the subject with the bed unit 106 being in the horizontal state. Furthermore, as described above, by moving the coupling unit 112 in the up-down direction, the operator can move components such as the bed unit 106 and the panel unit 120 (the display unit 122, the operation unit 124) in the up-down direction (the B direction, the C direction).

When a subject gets off from the bed unit 106, the operator brings the bed unit 106 into a reclined state (state in which a backrest is provided), as illustrated in FIG. 11. It is possible to make the subject easily get into or off from the bed unit 106.

FIG. 12 is a diagram illustrating a configuration in which a reclining direction of the bed unit 106 differs from that illustrated in FIG. 11.

In the configuration of the bed unit 106 that is illustrated in FIG. 11, the second frame 452 supports the upper body of a subject, but in the configuration of the bed unit 106 that is illustrated in FIG. 12, the second frame 452 supports the lower body of the subject. In addition, the third frame 454 supports the lower body of the subject, but in the configuration of the bed unit 106 that is illustrated in FIG. 12, the third frame 454 supports the upper body of the subject.

By the motor driving of the drive unit, the second frame 452 can be rotated in a predetermined rotational direction (I direction). As illustrated in FIG. 12, the operator can rotate the second frame 452 and tilt the second frame 452 downward. By tilting the second frame 452 downward, it is possible to lower the lower body of the subject.

In addition, by the motor driving of the drive unit, the third frame 454 can be rotated in a predetermined rotational direction (J direction). As illustrated in FIG. 12, the operator can rotate the third frame 454 and tilt the third frame 454 upward. By tilting the third frame 454 upward, it is possible to straighten up the upper body of the subject.

In addition, in the configuration of the panel unit 120 that is illustrated in FIG. 11, the operation unit 124 to be operated by an operator is installed on the left side, and the probe holder 126, the bottle accommodation unit 128, and the box 130 of tissue paper are installed on the right side.

The operation unit 124 is detachably attached to the panel unit 120. As illustrated in FIG. 12, the operation unit 124 can also be installed on the right side of the panel unit 120. In a similar manner, the probe holder 126, the bottle accommodation unit 128, and the box 130 of tissue paper are detachably attached to the panel unit 120. As illustrated in FIG. 12, the probe holder 126, the bottle accommodation unit 128, and the box 130 of tissue paper can also be installed on the left side of the panel unit 120.

In addition, in the configuration of the frame unit 140 that is illustrated in FIG. 11, the plurality of ultrasonic probes 142 is accommodated on the right side. The accommodation unit of ultrasonic probes is detachably attached to the frame unit 140.

As illustrated in FIG. 12, the accommodation unit of ultrasonic probes can also be installed on the left side of the frame unit 140.

As described above, the ultrasonic diagnosis apparatus according to the present invention includes the operation unit 124 that includes a plurality of input components, and inputs at least information regarding ultrasonic waves, the bed unit 106 on which a subject is to be placed, and the support unit 104 that supports the operation unit 124 and the bed unit 106 in such a manner that the operation unit 124 is arranged superior to the bed unit 106. The operation unit 124 is arranged at a position higher than a position at which the bed unit 106 is installed.

Because the operation unit 124 is installed superior to the bed unit 106, an operator can perform image capturing and operate the operation unit 124 in a natural posture with facing a subject placed on the bed unit 106.

The ultrasonic diagnosis apparatus according to the present invention also include the display unit 122 that displays an ultrasonic image that is based on ultrasonic waves transmitted and received using an ultrasonic probe that transmits and receives ultrasonic waves to and from a subject, and the support unit 104 supports the display unit 122 and the bed unit 106 in such a manner that the display unit 122 is arranged superior to the bed unit 106.

The support unit 104 in the ultrasonic diagnosis apparatus according to the present invention supports vertically-movably the operation unit 124 and the bed unit 106, and supports vertically-movably the display unit 122 and the bed unit 106.

The ultrasonic diagnosis apparatus according to the present invention includes an accommodation unit (the frame unit 140) that accommodates a plurality of ultrasonic probes. The support unit 104 supports the accommodation unit (the frame unit 140).

A computer program for implementing a control function (including various types of driving) of the ultrasonic diagnosis apparatus according to the present invention can be supplied to a computer (the control unit 18) of the ultrasonic diagnosis apparatus via a network or a storage medium (not illustrated), and the computer program can be executed.

The computer program is a program for implementing a function of the ultrasonic diagnosis apparatus in the computer (the control unit 18). The storage medium stores the computer program.

The present invention is not limited to the above embodiments and various changes and modifications can be made within the spirit and scope of the present invention. Therefore, to apprise the public of the scope of the present invention, the following claims are made.

According to the present invention, it is possible to improve the operability in an ultrasonic diagnosis apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An ultrasonic diagnosis apparatus comprising:
an operation unit including a plurality of input components, and configured to input at least information regarding an ultrasonic wave;
an accommodation unit accommodating an ultrasonic probe;
a drive unit moving the ultrasonic probe up and down;
a bed unit on which a subject is to lie; and
a support unit configured to support the operation unit, the bed unit and the accommodation unit such that
the operation unit is positioned above the bed unit,
the accommodation unit is positioned above the operation unit, and
each of the bed unit and the operation unit is movable up and down,
wherein the accommodation unit is arranged at a position in a horizontal direction where the ultrasonic probe and the operation unit do not interfere with each other when the ultrasonic probe comes down from the accommodation unit.

2. The ultrasonic diagnosis apparatus according to claim 1, further comprising a display unit configured to display an ultrasonic image that is based on an ultrasonic wave transmitted and received using an ultrasonic probe that transmits and receives ultrasonic waves to and from a subject, wherein the support unit supports the display unit and the bed unit in such a manner that the display unit is arranged superior to the bed unit.

3. The ultrasonic diagnosis apparatus according to claim 2, wherein the support unit supports the bed unit and the display unit in such a manner that the bed unit and the display unit are separated in an up-down direction.

4. The ultrasonic diagnosis apparatus according to claim 2, further comprising a panel unit including the operation unit and the display unit.

5. The ultrasonic diagnosis apparatus according to claim 4, wherein the operation unit is installed on the panel unit via an arm.

6. The ultrasonic diagnosis apparatus according to claim 5,
wherein the arm is installed on the panel unit via a first hinge portion,
wherein the operation unit is installed on the arm via a second hinge portion, and
wherein, by folding the arm, the operation unit is accommodated in the panel unit.

7. The ultrasonic diagnosis apparatus according to claim 6, wherein the first hinge portion is a torque hinge that can stop the arm at an arbitrary position.

8. The ultrasonic diagnosis apparatus according to claim 4, wherein the panel unit includes an ultrasonic probe holder for placing an ultrasonic probe, and a bottle accommodation unit that accommodates a bottle of ultrasound gel.

9. The ultrasonic diagnosis apparatus according to claim 4, wherein the display unit is installed rotatably relative to the panel unit.

10. The ultrasonic diagnosis apparatus according to claim 4, wherein the operation unit is detachably installed on the panel unit.

11. The ultrasonic diagnosis apparatus according to claim 2, wherein the display unit and the bed unit are supported by the support unit in such a manner that the display unit and the bed unit move in the up and down direction in a mutually-interlocked manner.

12. The ultrasonic diagnosis apparatus according to claim 2, further comprising a detection unit detecting body information of a user, and a control unit controlling to move the display unit and the operation unit in the up and down direction based on the body information.

13. The ultrasonic diagnosis apparatus according to claim 2, further comprising a control unit controlling to move the display unit and the operation unit in the up and down direction based on a setting information set by a user.

14. The ultrasonic diagnosis apparatus according to claim 1, wherein the support unit is a member extending in an up-down direction.

15. The ultrasonic diagnosis apparatus according to claim 1, wherein the support unit supports the bed unit and the operation unit in such a manner that the bed unit and the operation unit are separated in an up-down direction.

16. The ultrasonic diagnosis apparatus according to claim 1, wherein the support unit has a cantilever structure of supporting the operation unit and the bed unit in such a manner that the operation unit and the bed unit protrude toward one direction.

17. The ultrasonic diagnosis apparatus according to claim 1, wherein the operation unit is supported on the support unit via an arm.

18. The ultrasonic diagnosis apparatus according to claim 17, wherein the arm is extendable and contractible.

19. The ultrasonic diagnosis apparatus according to claim 1, further comprising a coupling unit configured to couple between the panel unit and the bed unit, wherein the coupling unit is supported movably in an up-down direction relative to the support unit.

\* \* \* \* \*